(12) United States Patent
McDaniel

(10) Patent No.: US 6,936,044 B2
(45) Date of Patent: Aug. 30, 2005

(54) METHOD AND APPARATUS FOR THE STIMULATION OF HAIR GROWTH

(75) Inventor: David H. McDaniel, Virginia Beach, VA (US)

(73) Assignee: Light BioScience, LLC, Virginia Beach, VA (US)

( * ) Notice: Subject to any disclaimer, the term of this patent is extended or adjusted under 35 U.S.C. 154(b) by 0 days.

(21) Appl. No.: 09/986,367

(22) Filed: Nov. 8, 2001

(65) Prior Publication Data

US 2003/0023283 A1 Jan. 30, 2003

Related U.S. Application Data

(60) Continuation-in-part of application No. 09/819,081, filed on Feb. 15, 2001, now Pat. No. 6,629,971, which is a division of application No. 09/203,178, filed on Nov. 30, 1998, now Pat. No. 6,283,956.

(51) Int. Cl.[7] .............................................. A61B 18/18
(52) U.S. Cl. ............................ 606/9; 606/10; 607/88; 128/898
(58) Field of Search ................................. 606/9–13, 16, 606/32–34, 127, 128, 41, 131–134, 187; 607/88–91; 128/898

(56) References Cited

U.S. PATENT DOCUMENTS

| 5,071,416 A | | 12/1991 | Heller et al. | |
|---|---|---|---|---|
| 5,647,866 A | * | 7/1997 | Zaias et al. | 606/9 |
| 5,752,949 A | * | 5/1998 | Tankovich et al. | 606/9 |
| 5,766,214 A | * | 6/1998 | Mehl, Sr. et al. | 606/9 |
| 6,050,990 A | * | 4/2000 | Tankovich et al. | 606/9 |
| 6,074,382 A | | 6/2000 | Asah et al. | |
| 6,283,956 B1 | * | 9/2001 | McDaniel | 606/9 |
| 6,497,719 B2 | | 12/2002 | Pearl et al. | 607/89 |

OTHER PUBLICATIONS

Hair Regrowth with Cell–wave Therapy; A Guide to treatment, 1996.*
'Laser Hair Care,' Model 4000, 1996. www.laserhaircare.com/laserhair/background.html.*
Des Travers, Australasian Post, Feb. 11, 1989.
Hair Regrowth with Cell–wave Therapy: A guide to treatment, 1996.
Pontinen et al. The Effect of Hair Lasers on Skin Blood Flow, Acupuncture & Electrotherapeutic Res. Int. J., vol. 21, pp. 105–118 (1996).
http://www.laserhaircare.com/laserhair/background.html (citing early model laser hoods).

* cited by examiner

*Primary Examiner*—A. Farah
(74) *Attorney, Agent, or Firm*—Morrison & Foerster LLP

(57) ABSTRACT

A method and apparatus for producing hair growth stimulation using light energy, topical compositions, and combinations thereof. By using photomodulation resulting from cellular responses to exposure to specific wavelengths of light, optionally in conjunction with topical compositions and procedures for enhancing the penetration of such compositions, hair follicles are activated to produce hair growth.

2 Claims, 15 Drawing Sheets

HAIR GROWTH

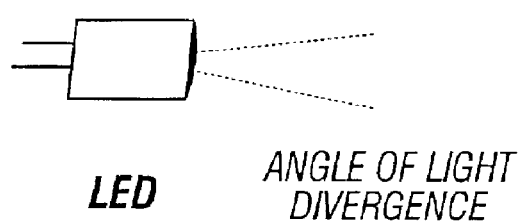
LED  ANGLE OF LIGHT DIVERGENCE
FIG. 10A
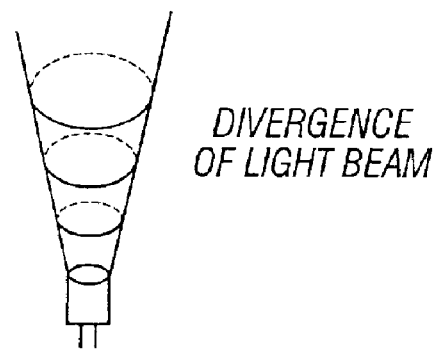
DIVERGENCE OF LIGHT BEAM
FIG. 10B
FIG. 11A
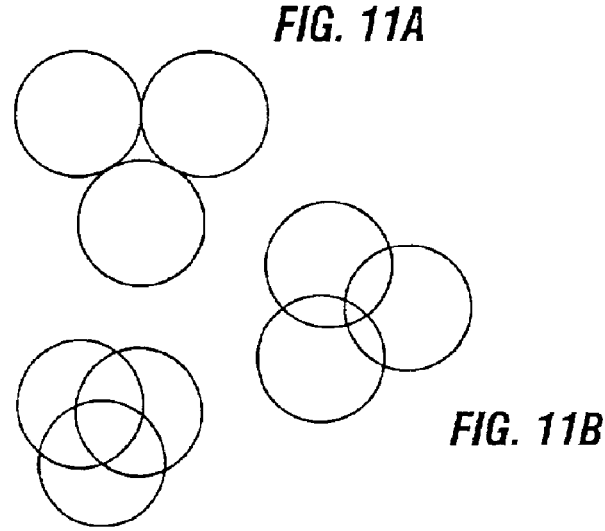
VARIOUS BEAM PATTERNS
FIG. 11B
FIG. 11C

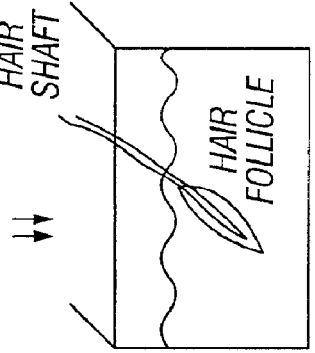
FIG. 14A PSORIASIS
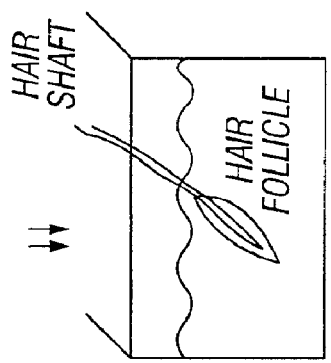
FIG. 14B HAIR GROWTH (HAIR SHAFT, HAIR FOLLICLE)
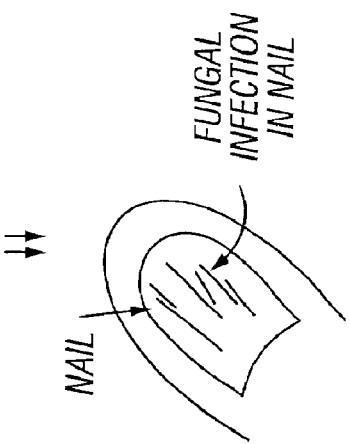
FIG. 14C HYPERTROPHIC SCAR
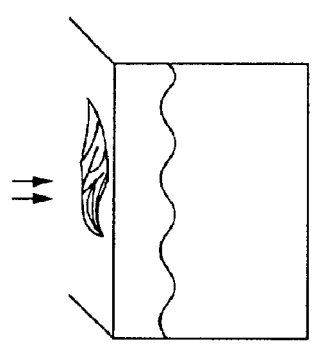
FIG. 14D ACNE (SEBACEOUS OIL GLAND, EXOGENOUS CHROMOPHORE)
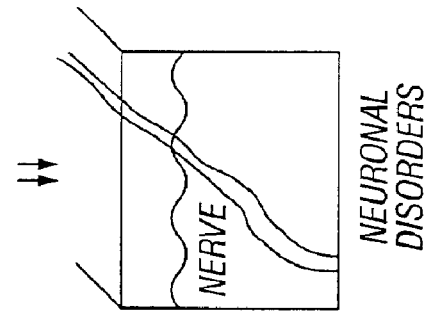
FIG. 14E NEURONAL DISORDERS (NERVE)
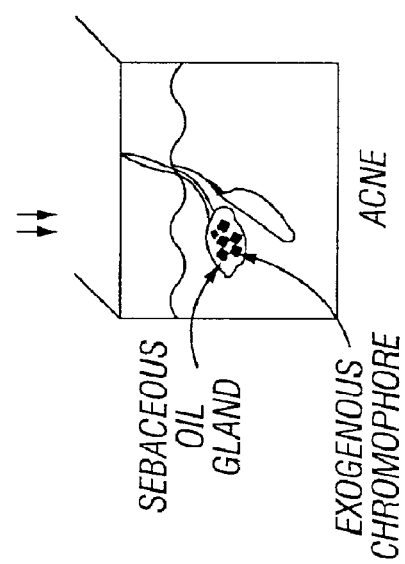
FIG. 14F (NAIL, FUNGAL INFECTION IN NAIL)

US 6,936,044 B2

METHOD AND APPARATUS FOR THE STIMULATION OF HAIR GROWTH

This application is a continuation-in-part of U.S. application Ser. No. 09/819,081, filed Feb. 15, 2001, now U.S. Pat. No. 6,629,971, which is a divisional application of U.S. application Ser. No. 09/203,178, filed Nov. 30, 1998 now U.S. Pat. No. 6,283,956.

FIELD OF THE INVENTION

The present invention generally relates to a system and method for the stimulation of hair growth, using a novel combination of photothermal, photochemical and photomodulatory alone or by also applying a drug or a cosmeceutical composition, naturally occurring chromophore, or other light-activated chromophore to or into the hair follicle hair bulb, hair bulge, hair stem cell or surrounding tissue and exposing the composition to electromagnetic radiation.

BACKGROUND OF THE INVENTION

There are several known techniques for attempting to reduce or eliminate hair growth in human skin. A few of these known techniques such as topical minoxidil or the commerically available product "Rogaine" are scientifically proven and widely accepted as effective. However, their degree of efficacy varies greatly.

There are several processes which may be used for producing preferential damage of the hair but relatively few are known which stimulate hair growth. In one process the target may be natural melanin pigment in the hair shaft and surrounding supporting tissues. In another process the target may be an external chromophore or contaminant. Most of these processes tend to damage the hair, either by producing heat or by photo-acoustical shock waves. These known processes have varying degrees of effectiveness, but require multiple treatments and, in their current form, produce only partial permanent hair reduction.

In recent years the use of light sources to reduce or eliminate unwanted hair growth has been developed. One known technique selects a wavelength of laser light that is well-absorbed by the naturally occurring "native" pigments in the hair shaft (and perhaps some pigment in parts of the hair duct or hair follicle cells).

Another known technique uses a short pulsed laser to produce a wavelength that may be absorbed by a "foreign" material or "skin contaminant". Aspects of this technique are described, for example, in U.S. Pat. Nos. 5,423,803, 5,817,089, 5,425,728, 5,226,907, and 5,752,949, all of which are incorporated by reference. This contaminant may be applied directly onto the skin and may be introduced into the empty space surrounding the hair shaft. One contaminant that has been used is carbon graphite in particulate form. The graphite particles have a diameter that is small enough to enable the particles to drop from the surface of the skin into the free empty spaces between the duct and the hair shaft. The energy from a laser may then interact with the contaminant particles. This causes injury to surrounding tissues whose function is to support the growth of the hair shaft. This tends to reduce or eliminate hair growth.

These contaminant particles are not physically incorporated into the hair shaft or into the surrounding hair follicle, hair bulge or hair duct cells. Nor do these contaminant particles chemically, immunologically, biologically or otherwise interact, react or complex with the hair shafts or tissue cells. The contaminant particles simply physically occupy the space surrounding the hair shaft.

Another known hair removal technique is to use a pulsed electromagnetic radiation source to produce a wavelength that may be absorbed by hair, as described, for example, in U.S. Pat. No. 5,683,380, which is incorporated by reference.

There are problems with present light and laser hair removal techniques. Known melanin targeting systems work reasonably well and are reasonably safe only when the color of the hair is very dark and when the skin is very light and not tanned. Virtually all light sources which tend to target melanin are also inherently absorbed by the overlying and surrounding skin. At present, these light sources cannot be safely used at optimal very high power settings for people with darker skin or even people with a dark tan.

Dying the hair allows increased damage to the hair target, helps confine damage to the hair target, and enables the use of power settings that are not so high as to damage surrounding and overlying skin. Treatments which target melanin inherently do not work well on light hair, since there is not enough natural pigment to absorb enough energy to damage hair even if the power is quite high. Using hair dye enables this obstacle to be overcome.

A known hair removal process which uses a 1064 nm laser to produce a wavelength that may be absorbed by a skin contaminant appears to be safe on all skin colors, including darker skin colors. However, this safety is a consequence of there being very little melanin absorption. It is therefore necessary to add graphite particles in oil contaminant lotion before laser treatment. This graphite particle lotion does not enter into the hair shaft itself. Instead, the graphite lotion tends to occupy empty spaces surrounding the hair shaft as it sits in the hair duct. This presents a problem. Either an insufficient or sub-optimal number of graphite particles penetrate into the hair duct, or an insufficient amount of damage is caused by the graphite particles. Consequently, many treatments tend to be required before an acceptable result is achieved.

SUMMARY OF THE INVENTION

The present invention relates to a method for stimulating hair growth in which the a hair growth structure is exposed to a source of electromagnetic radiation having a dominant emissive wavelength of from about 390 nm to about 1600 nm. By way of definition, the dominant emmisive wavelength is the primary wavelength emitted by the source of electromagnetic radiation, i.e., that wavelength is emitted at a greater intensity than any other wavelength. Photostimulating the hair growth structure is then performed by maintaining the exposure of the hair growth structure to the source of electromagnetic radiation for a clinically effective duration and at a clinically effective light intensity. Clinically effective durations and intensities are further described in the detailed description of the invention and examples and can include single pulses from a single source of electromagnetic radiation, multiple pulses from a single source of electromagnetic radiation, multiple pulses from multiple sources of electomagnetic radiation, single pulses from multiple sources of electromagnetic radiation, simultaneous pulses from multiple sources of radiation, and combinations thereof.

The exposure to electromagnetic radiation may be enhanced by way of the use of penetration enhancing agents or photomodulating agents. Exemplary of such agents, whose function is to enhance are selected from the group consisting of at least one of Vitamin C, Vitamin E, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, an antioxidant, a phytoanthocyanin, epigallocatechin-3-gallate, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, minoxidil, a hair growth stimulating substance, a hair growth inhibiting substance, a dye, a natural or synthetic melanin, a metalloproteinase inhibitor an inhibitor of AP-1 or c-Jun, proline, hydroxyproline, an anesthetic substance, chlorophyll, copper chlorophyllin, chloroplasts, carotenoids, bacteriochlorophyll, phycobilins, carotene, xanthophyll, anthocyanin, and derivatives, subcomponents, and analogs of the above, both natural and synthetic, and mixtures thereof. The list is meant to be illustrative and not exhaustive, as those of ordinary skill in the art will recognize, based on the disclosure herein, that other compounds are capable of treating the upper layers of the skin, hair structures, and surrounding tissue to enhance treatment with electromagnetic radiation.

Further, physical procedures may be performed to permit greater penetration of electromagnetic radiation into target hair structure, skin, and surrounding tissue in preparation for treatment. Such procedures include, but are not limited to: enzyme peel, microderm abrasion, solvent stripping, tape stripping, scrubbing, laser ablation, laser vaporization, chemical peeling, electrical stimulation, laser treatments using high peak power and short pulse durations, ultrasound, or combinations thereof.

Finally, the source or sources of electromagnetic radiation for use with the present invention are essentially unlimited. The criteria for selection of the source is treatment-dependent and is only limited to emitters of electromagnetic radiation in the range of from about 300 nm to about 1600 nm, either directly or after mechanical or electrical filatration of the radiation. Most preferred among such emitters, due to their cost and availability are light emitting diodes (LED's), lasers, flashlamps, fluorescent lights, dye lasers, diode lasers, and incandescent sources filtered to produce a dominant emissive wavelength in the desired range.

BRIEF DESCRIPTION OF THE DRAWINGS

FIGS. 10A–10B illustrate examples of individual LEDs in accordance with the present invention and the angle of divergence of an emitted beam.

FIGS. 11A–11C illustrates three different examples of patterns of light energy density on the field of illumination. The irradiation illustrated in FIG. 18B is relatively uniform and homogeneous. The irradiation illustrated in FIG. 18C is relatively uneven and non homogeneous.

FIG. 14A illustrates an example of use on skin diseases such as psoriasis (a proliferative skin disorder that is known to respond to ultraviolet light therapy).

FIG. 14B illustrates applications of the present invention to delay, stimulate or inhibit hair growth.

FIG. 14C illustrates the treatment of scars or stretch marks is also possible

FIG. 14D shows the use of LED light in conjunction with an exogenous chromophore to diminish oil gland activity or to reduce acne.

FIG. 14E illustrates an example of illumination by the LED of nerve fibers where nerve injuries need to be stimulated, regenerated, or healed.

FIG. 14F illustrates nail disorders with fungal infection, to be treated in accordance with the present invention.

Figure 1A:
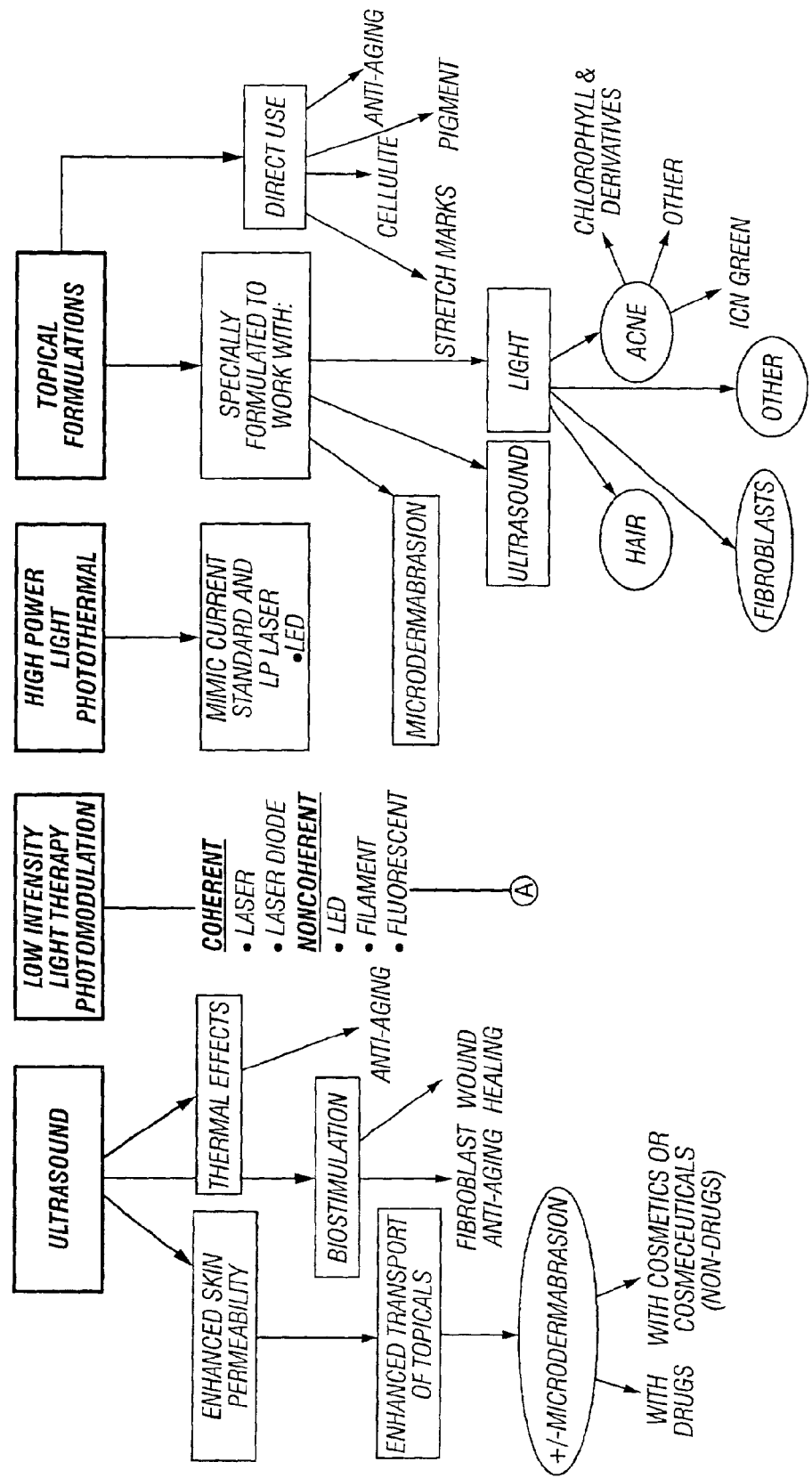
FIGS. 1a and 1b are schematical illustrations of various treatment regimens, including the low level light method of the present invention which may also incorporate the use of topical formulations.
Figure 1B:
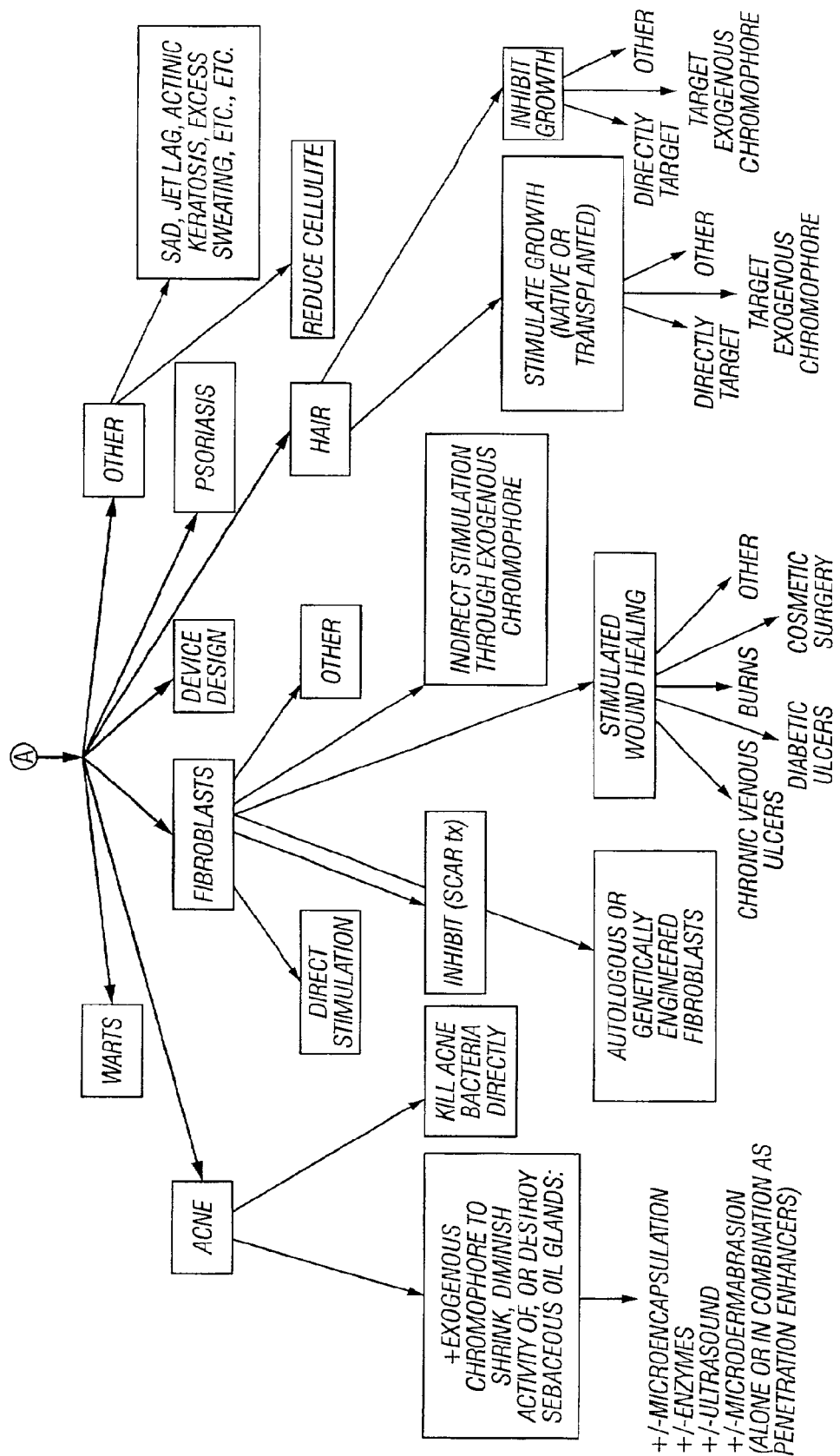
Figure 2A:
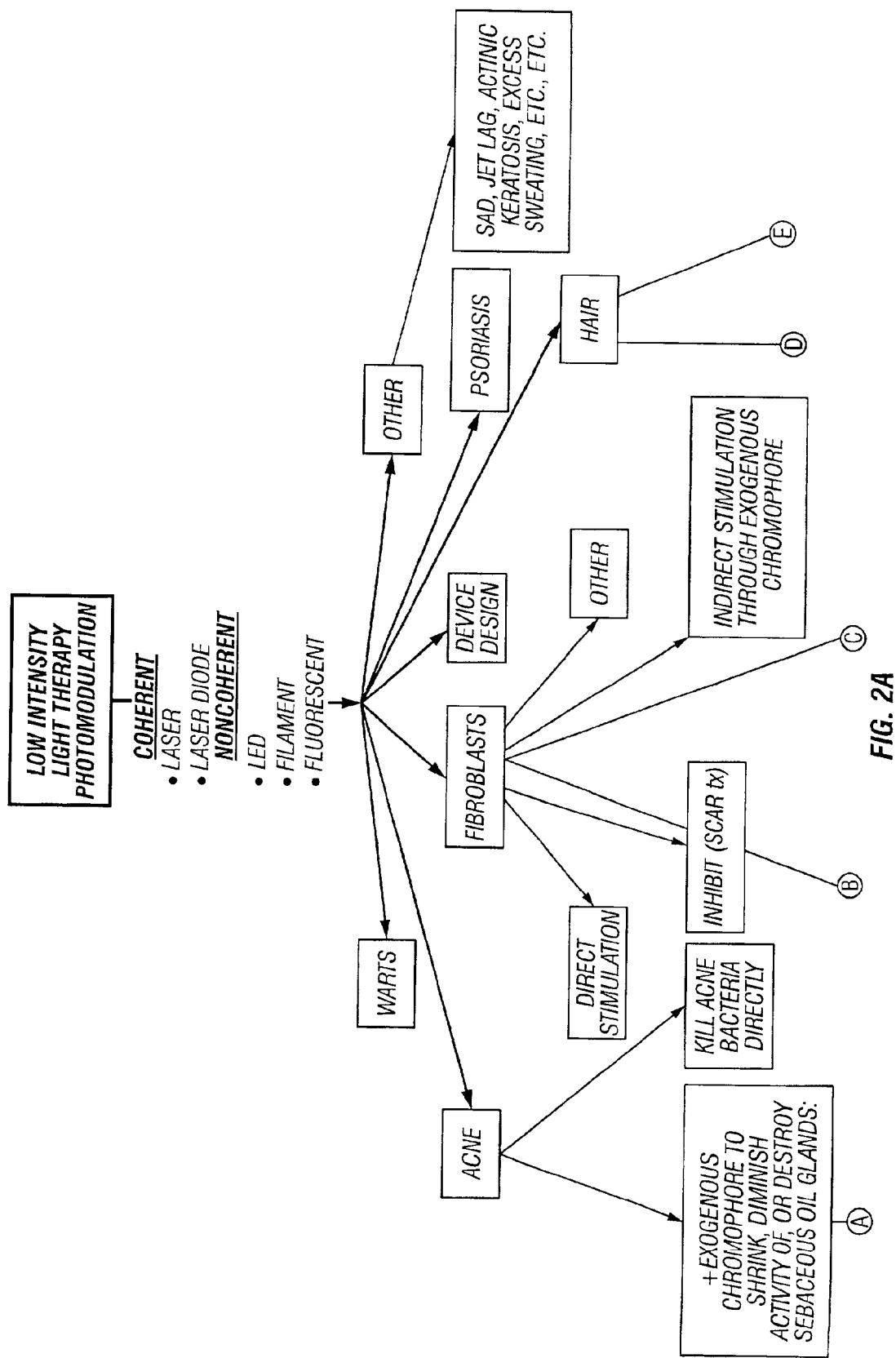
FIGS. 2a and 2b combine to form a schematical representation of treatment regimens pertaining to the use of low level light according to the present invention.
Figure 2B:
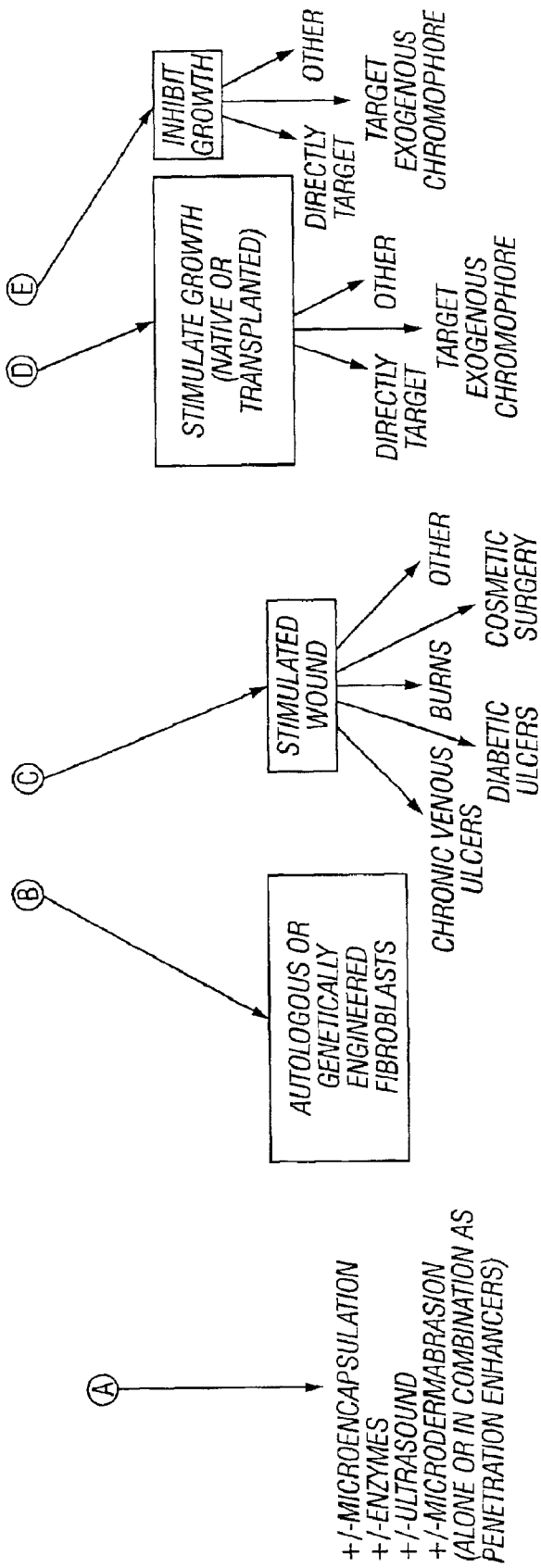

The detailed description of a preferred embodiment of the present invention will be made with reference to the accompanying drawings.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

In a preferred embodiment, the present invention is directed to a process for dermatological treatment. Such a treatment may include the photomodulation of hair follicles, hair bulb, hair bulge, stem cells and the surrounding tissue to produce temporary or permanent stimulation of activity of surrounding tissue or supporting tissue in human or mammalian skin, of some or all of the hairs. In a preferred embodiment the process produces little or no permanent injury or damage to nearby skin tissue. Primarily, only the hair and immediately surrounding tissue are affected. For purposes of the present invention, any recitation of the hair also includes the hair follicle, bulb, bulge, stem cells and other components of the supporting dermal structure that supports hair growth.

In a process according to one embodiment of the present invention, an agent may be selected which is capable of penetrating the hair ducts and attaching, bonding or otherwise becoming incorporated into the hair shaft, hair follicle, hair bulb, hair duct cells, or stem cells collectively referred to hereinafter as hair growth structures. The agent may be characterized as an active agent in that it performs a function in addition to simply occupying or contaminating the space in the ducts surrounding the hair shaft. The agent may have sufficient optical absorption of a wavelength (or a combination of wavelengths) of a coherent or non-coherent light source which can penetrate the skin adequately to be absorbed by the target agent or the new agent-tissue complex or it may in some other way directly or indirectly enhance the stimulatio of hair growth structures.

The area of skin overlying where the hair duct is located may be cleansed. After the skin is cleansed, the skin may be treated to improve permeability. This may be accomplished, for example, by treating the skin with steam or a hot moist towel to hydrate the skin and hair or removing a portion of the stratum corneum through various means known in the art, exemplary of which is microdermabrasion.

The agent may be applied in sufficient quantity and in suitable form to be incorporated into the target tissue in adequate or optimal amounts to allow the production of the desired tissue effect, as described in U.S. Pat. No. 6,283,956 which is hereby incorporated by reference in its entirety.

Excess agent may be removed, neutralized, inactivated, decolorized, diluted or otherwise altered so that residual contamination of the skin by such excess agent is either (a) absent and does not interact with the light or energy source, or (b) present in such small quantity that it provides no clinical effect.

Delivery of the desired agent into the target tissues, ducts, or nearby sebaceous oil glands may be enhanced, facilitated or made possible by the use of enzymes capable of altering the structure, permeability, or other physical characteristics of the stratum corneum or by the use of ultrasound or phonophoresis either for penetration into the gland or surrounding target tissues or, once penetrated, to cause the release of the agent from the encapsulated delivery device such as liposomes, polymers, microspheres, etc. so as to cause penetration or attachment of this active agent. Ultrasound may be used therapeutically to interact directly with the agent or the agent-tissue complex to produce the desired damaged target tissues (to be used alone or in combination with laser or non-laser light sources). Microdermabrasion may also be used to permit greater penetration of the skin, wherein the upper epithelial layers are removed. These layers create a natural barrier to the permeability of the skin and, by their removal, penetration of the skin by topical agents is facilitated. This method may be further enhanced by using ultrasound, alone or in combination with alteration of the stratum corneum, to further improve the performance of topical compositions. A more detailed description of several aspects of the use of ultrasound may be found, for example, in the applicant's U.S. Pat. No. 6,030,374 for "Ultrasound Enhancement of Percutaneous Drug Absorption" which is hereby incorporated by reference in its entirety. Further, methods of improving the penetration of topical agents through the stratum corneum are more fully described in applicant's copending U.S. application Ser. No. 09/876,157, which is hereby incorporated by reference.

Although preferred embodiments of the present invention may use LEDs, ultrasound and/or laser or light energy from sources such as light-emitting diodes, the present invention is not limited to the use of these energy sources. Other sources of energy, including (without limitation) microwave energy and radio frequency energy or electrical stimulation or magnetic fields/forces may also be used. Exemplary of known light sources are fluorescent lights, flashlamps, filamentous lights, metal halide lights, halogen lights, etc. One skilled in the art will recognize that any light source capable of emitting electromagnetic radiation at a medically useful wavelength, as described herein, directly, or by means of optical filtration, is within the scope of suitable light sources according to the present invention. For purposes of the photomodulatory and photothermal treatment methods described, any source capable of emitting light having a wavelength from about 300 nm to about 1600 nm, or producing electromagnetic radiation which is filtered or otherwise altered to expose the skin, a topical composition, or other component of the present treatment regime to a wavelength of light in the aforementioned range is medically useful.

Figure 3:
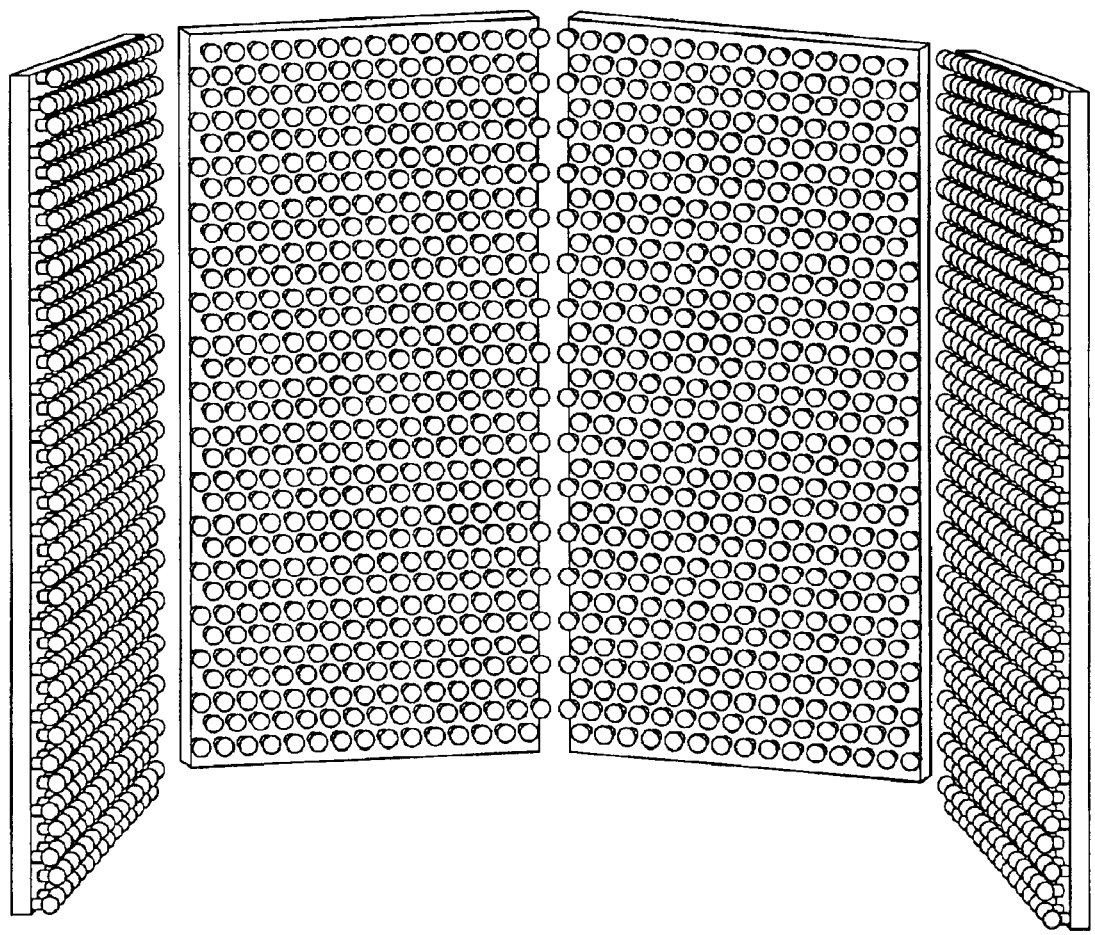
FIG. 3 is an illustration of an embodiment of an LED array of the present invention having multiple panels of arrays.
Figure 4:
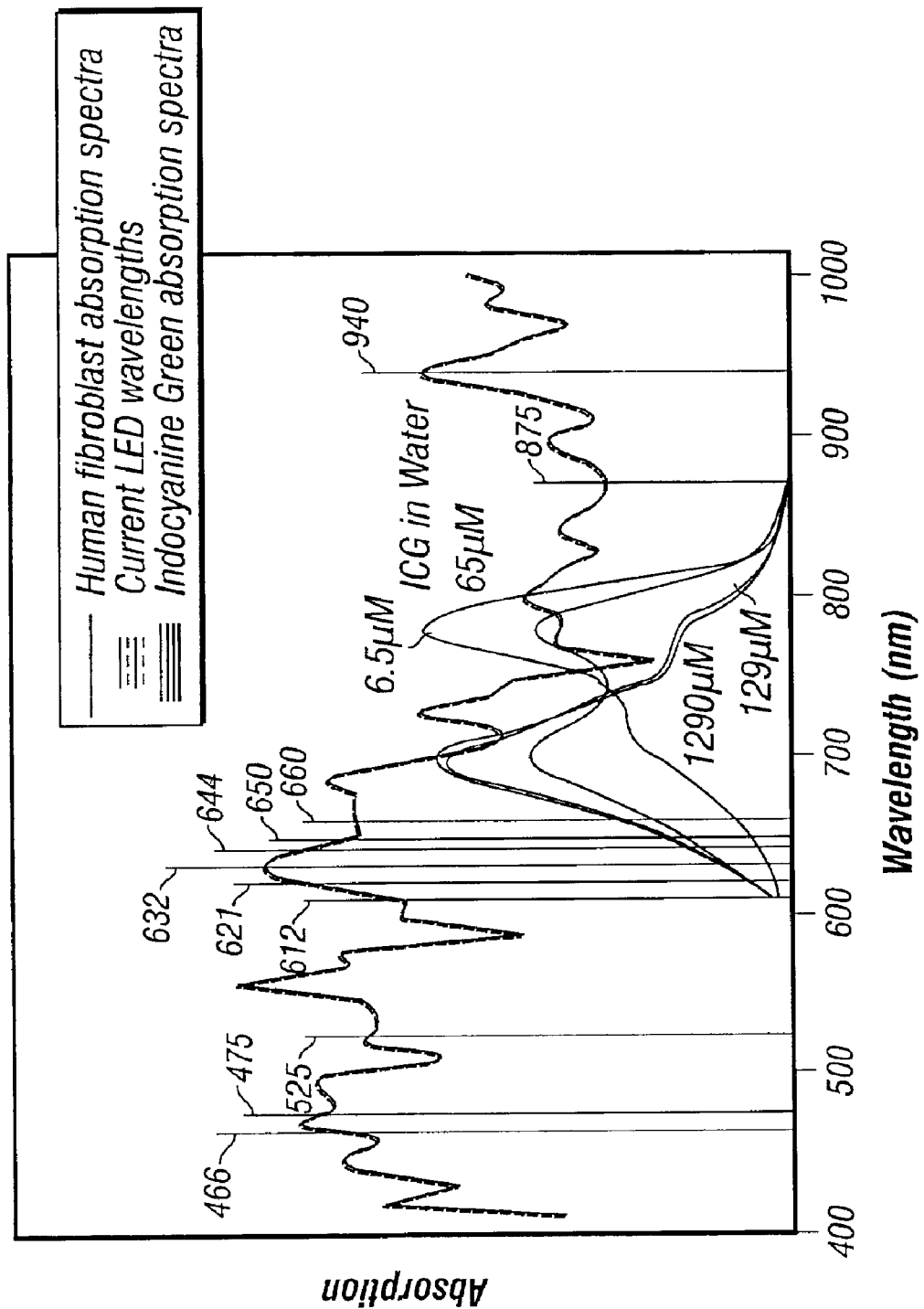
FIG. 4 is a graphical illustration of the absorption spectrum of human fibroblast overlayed with the wavelengths used by narrowband, multichromatic LED emitters of the present invention and also the absorption spectrum of indocyanine green (ICG).
Figure 5:
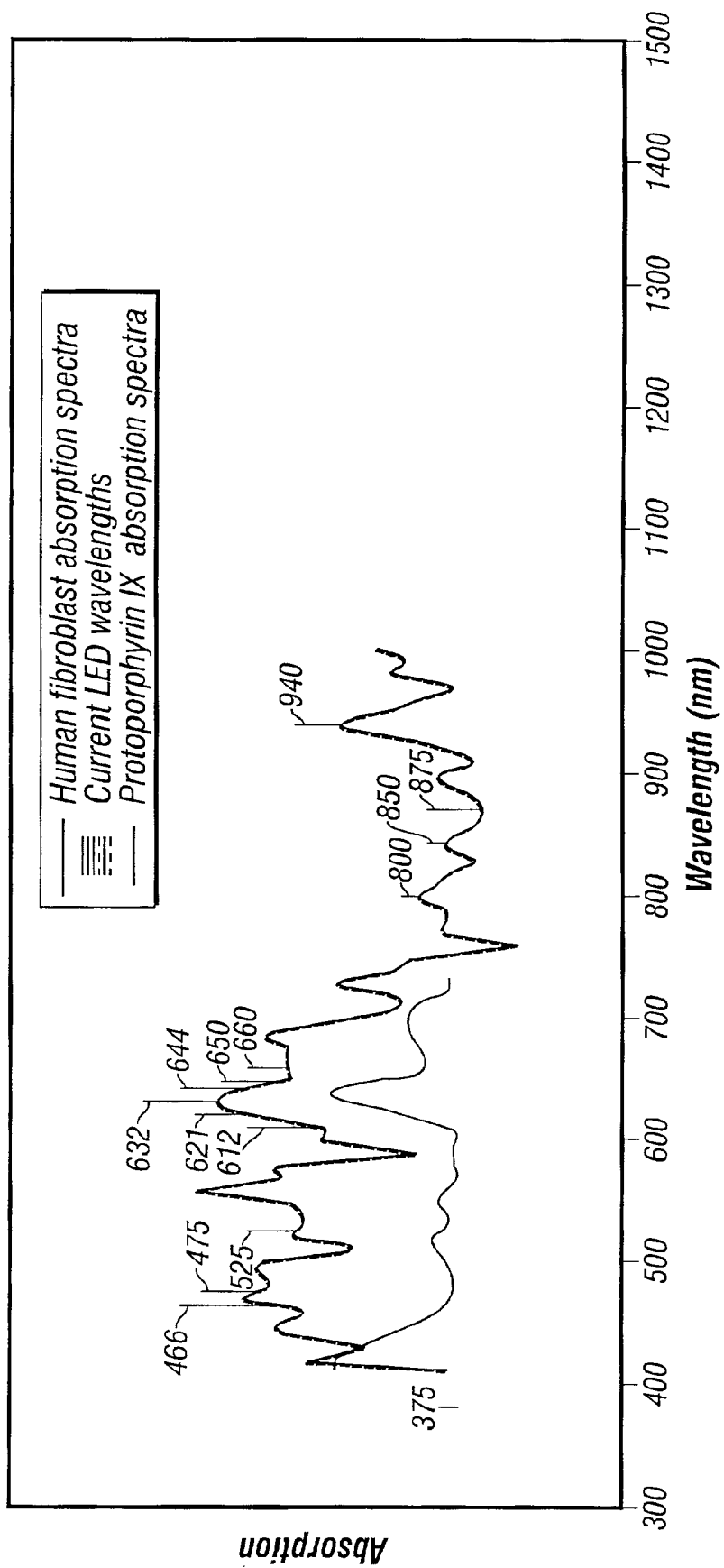
FIG. 5 is a graphical illustration of the absorption spectrum of human fibroblast overlayed with the wavelengths used by narrowband, multichromatic LED emitters of the present invention and also the absorption spectrum of protophorphyrin IX, one of the active chromophores in acne bacteria.
Figure 9:
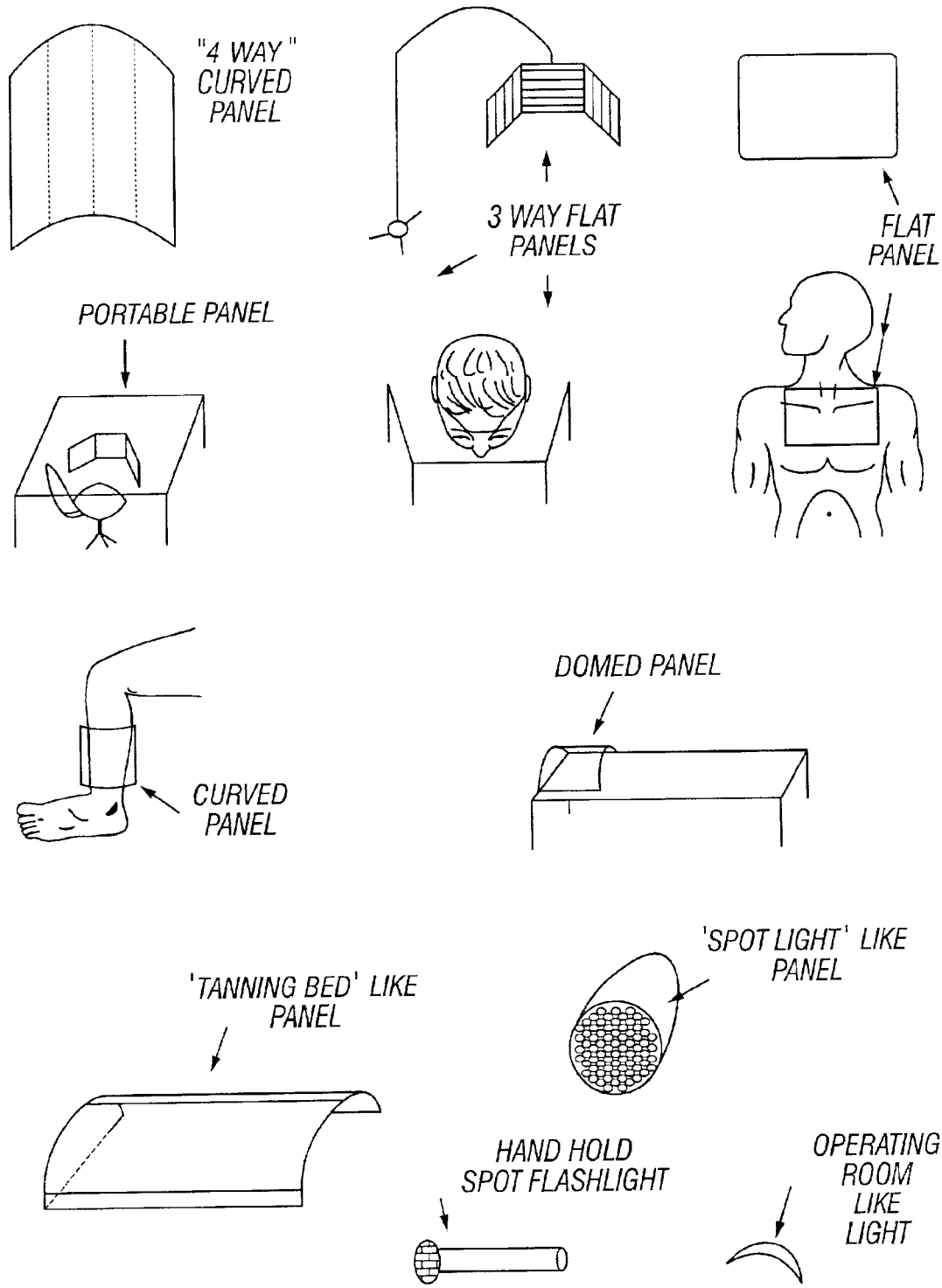
FIG. 9 is an illustration examples of possible configurations of arrays for various treatment applications.
Figure 12:
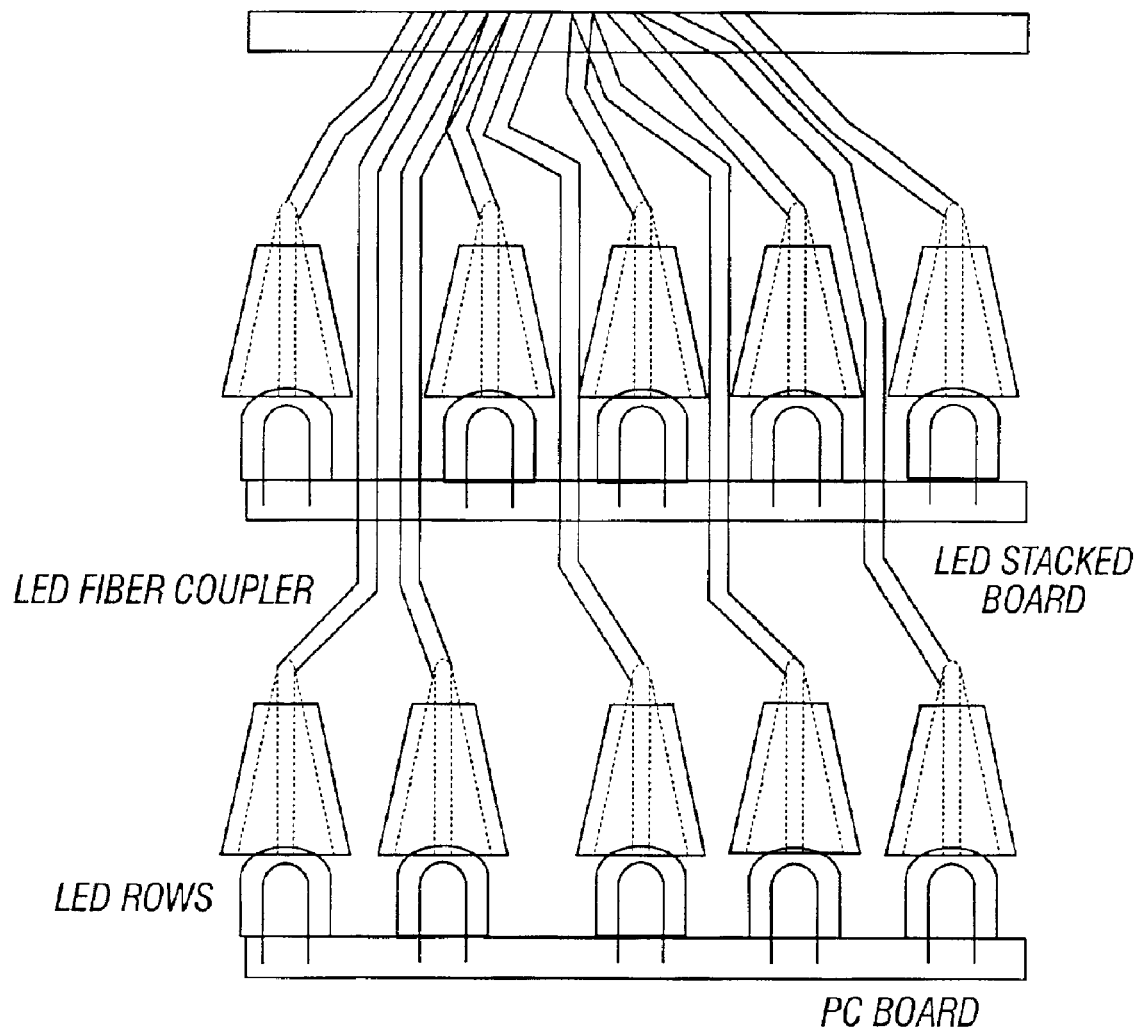
FIG. 12 is a shows a technique for coupling the light output of an optoelectronic device with an optical fiber.
Figure 13:
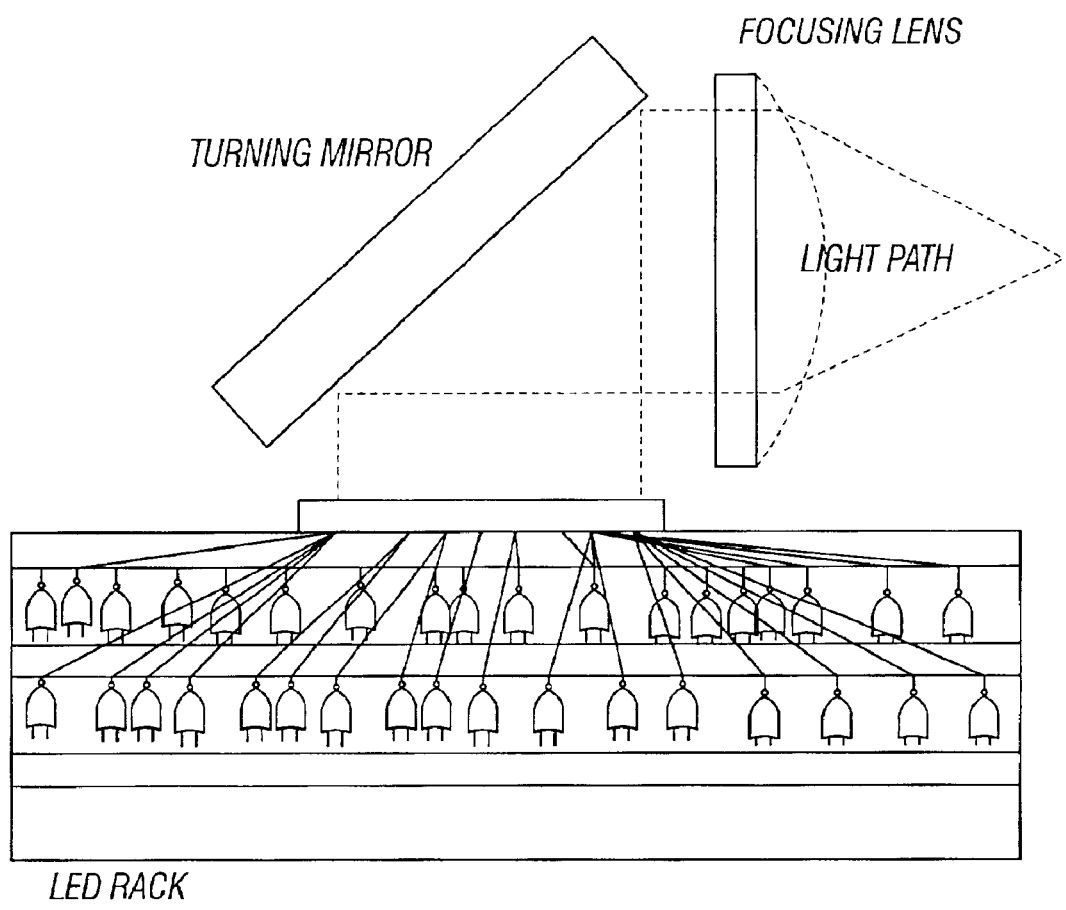
FIG. 13 is a schematic drawing of the output of several individual optoelectronic devices collected into a single beam.

The targeted skin may be exposed to one or more wavelengths of LED, laser or non-laser light such as filtered filamentous sources or fluorescent sources alone or in combination with single or multiple frequencies of ultrasound. The light source may be polarized or unpolarized, as can any light source described herein in accordance with the present invention. A variety of parameters may be used (including pulse duration, energy, single or multiple pulses, the interval between pulses, the total number of pulses, etc.) to deliver sufficient cumulative energy to interact with the agent or tissue complex. One embodiment of the invention, this results in the stimulation of hair growth or the supporting skin tissue through photomodulatory means, photothermal means electrical stimulation, or combinations thereof. Alternatively, proper exposure to certain wavelengths of light, combinations of certain wavelengths of light, such light sources either alone in combination at various intensity levels, with and without topical compositions to enhance the penetration of the light, are capable of photostimulation of hair follicles, glandular and duct activity, etc. resulting in the stimulation of hair growth. Ultrasound may also be used to preheat the target structures or the entire skin. Further for treatment over a broad area of human skin, the light source may be diffused through a device such as a holographic diffuser; or, alternatively, the light source may be comprised of an array of individual emitters such as the multi-panel array of LEDs illustrated in FIG. 3. Further increasing the number of panels to more precisely follow the contours of the portion of the patient receiving treatment produces more uniform exposure and improved results. For example, a collection of panels that can be manipulated to provide even exposure to the entire face or scalp of a patient will provide excellent results when the facial area is targeted to reduce facial hair or when the scalp is treated to stimulate hair growth. For localized treatment, smaller arrays or individual LEDs, such as in the hand held devices. A collage of such devices is illustrated in FIG. 9 Since LED sources are generally considered "insignificant risk devices", no medical supervision is required and these devices may be used by the patient for at-home treatment or as part of an ongoing skin-care system after receiving treatment by a physician.

The topical agent may be incorporated into the target tissue by a variety of mechanisms. These mechanisms include, but are not limited to: 1) physical incorporation into target tissue cells while leaving the chemical structure essentially unaffected, or 2) undergoing a chemical reaction resulting in a new agent-tissue complex which then becomes a target for energy absorption.

The process may be a single or multi-step process and may involve the use of cofactors, catalysts, enzymes, or multiple agents which interact to ultimately become or create an active agent or agent-tissue complex.

Agents may include, without limitation, the following compositions and derivatives and analogs thereof: hair dyes, vegetable dyes, food coloring, fabric dyes, tissue stains, shoe or leather dyes, other plant products (such as flavonols, chlorophyll, copper chlorophyllin, bacteria chlorophylls, carotenoids, enzymes, monoclonal antibodies, any immunological agent, genetically engineered agent, benign infectious agents, whether naturally occurring or genetically engineered (e.g. the bacteria that normally reside on the skin such as acne bacteria, etc.), antibiotics, agents which attach to sebocytes in the sebaceous gland or duct cells directly, whether by topical or systemic agents that localize in these target tissues, including antibodies or antibody-chromophore compounds of these structures. The preceding list is illustrative and not exhaustive of those agents suitable for use in accordance with the present invention. In general, the topical agent chosen will have certain absorption characteristics that augment the penetration of the radiation to the tissue targeted for treatment, i.e., or increasing blood circulation to the structures. Additional agents that are most beneficial for stimulating hair growth have been found to include vasodilators, inhibitors of 5-alpha reductase (most preferably type 2, although type 1 is considered beneficial as well), stimulators or activators of ornithine decarboxylase, stimulators or activators of vascular endothelial growth factor (VEGF), PDGF, HGF, KGF, IGF, EGF, TGF-alpha, TGF-beta, FGF-alpha, FGF-beta, inhibitors of protein kinase C, stimulators or activators of adenylate cyclase, skin irritants, curcumin, mineralocorticoid receptor antagonists, and the various means known in the art for increasing intracellular $Ca^{2+}$ or any means of inhibiting MMP, AP-1, c-Jun in combinations with light. While the primary method of delivery for such agents is through topical contact with the skin, in some instances it is preferable or advantageous to administer the composition orally or by injection or other systemic route.

Most preferable are topical compositions that stimulate or modulate ornithine decarboxylase or vascular hair related growth factors or signaling molecules.

Agents may be delivered in pure form, in solution, in suspension, in emulsions, in liposomes, in synthetic or natural microspheres, microsponges or other known microencapsulation vehicles, alone or in combination or in other forms common or known to those skilled in art of topical and oral delivery. This list of the forms of the agents is illustrative and not exhaustive. Those skilled in the art will recognize that there are a wide variety of forms for the delivery of these types of compositions suitable for use in accordance with this invention.

The process may include an application of an active agent and treatment with an energy source as a single treatment. Alternatively, treatment with an energy source may be delayed for hours or days after application of an active agent. Application of an active agent may be performed or applied at another location, such as patient's home, prior to the energy treatment.

After an energy treatment has occurred it may be desirable in some situations to remove, neutralize, decolorize or otherwise inactivate any residual active agent. In other situations, continued application to replenish depleted chromophore may be desirable.

One hair reduction treatment process uses a solution of graphite in a carrier solution and a Q-switched 1064 nm ND:YAG laser. The solution may be applied to the skin which is then treated with the laser using known parameters. It may be preferable to use a high repetition rate and move the laser hand piece slowly enough that pulses are "stacked" in one spot for several pulses before the hand piece is moved to an adjacent spot. It has been found that there is a stair-step like effect of incremental temperature rise in the sebaceous glands with the second and third pulses versus a single pulse. A faster repetition rate also tends to help build the heat up faster, and to higher levels. This tends to produce the maximum heat (which is desirable, as long as the heat stays confined to the sebaceous glands and the immediately adjacent supporting tissues). Since this effect occurs substantially simultaneously with other destructive effects of the process, the damage to hair structures tends to be enhanced. Unlike carbon exploded particles on light impact, the dyes and similar agents may actually remain absorbing for a brief time until they reach a critical temperature at which time they are destroyed or become non absorbers, thus acting as a sort of heat sink for a brief time, allowing more heat to accumulate than with carbon solutions and short pulsed Q-Switched lasers. Safety remains at about the same level, since dye related damage tends to be confined to target tissues. There is no appreciable change in patient treatment time.

Another preferred embodiment uses a longer pulsed laser in the 750 nm–1000 nm range and appropriate parameters to achieve the desired tissue damage goal.

Another embodiment uses a tissue dye which attaches to, or is incorporated into, a target cell and surrounding tissues. The target tissue may be illuminated with a multi-wavelength non-laser light source using appropriate parameters to achieve the desired tissue stimulation goal.

Another embodiment uses a light source which is well-absorbed by the melanin naturally present in skin and undyed darker hairs. Natural or synthetic melanin or derivatives thereof will be well-absorbed by the same wavelength of light (or alternatively two or more wavelengths, one for melanin and one or more for the dye). This tends to benefit people having darker skin or tanned skin, by allowing lower treatment energy. For example, a diode laser or LED or non-laser light source could produce a continuous or pseudo-continuous beam of light energy using pulse durations as long as seconds at a wavelength which is absorbed by the light-activated chromophore or naturally occurring synthetic melanin delivered topically to the hair and supporting dermal structure. A pulse duration on the order of between about one and thirty seconds appears to be preferable. This also tends to be a much longer time than is used in most systems in use today.

Another embodiment uses an agent which facilitates cavitation shock waves or a thermal effect or both. This preferentially stimulates the target tissues while minimizing damage (or other adverse effects) on surrounding non-target tissues. This may be used with very short pulsed lasers or light sources or with ultrasound alone.

In one embodiment a process in accordance with the present invention may be used to provide short or long-term thickening darkening or stimulation of growth of hair. An active agent may be physically or chemically or immunologically incorporated into cells of the hair or nearby sebaceous (oil) glands, ducts, or supporting tissue, naturally occurring light activated chromophores. Some acne bacteria may not inhabit all sebaceous structures and other strains may not produce native porphyrins to target with light. Other acne bacteria may be located deeper than 400 nm to 420 nm light can adequately penetrate, thus treatment with light alone may be only partially effective in clinical treatment or longer deeper penetrating wavelengths such as yellow or red visible or infrared light may be used alone or in combination with the 400–420 nm blue visible light. Since acne bacteria are anerobic, that is they grow in the absence or relative absence of oxygen, introducing oxygen into the sebaceous apparatus or gland is toxic or destructive to these bacteria. Thus a light activated agent releasing oxygen or a topical adjunctive oxygen releasing or generating agent will also improve acne reduction treatment. Improvement in skin disorders may be a direct or indirect result of the application of the agents in this process, as may reduced oiliness of the skin, reduced size or diminished appearance of pores, etc. The present invention is also useful for treating enlarged pores, oily skin, stretch, marks, wound healing (alone or in combination with growth factors) and other disorders where there is no active acne-related disorder. Other similar disorders such as folliculitis which involve the pilosebaceous (hair/oil gland) unit may also be treated using the present invention. The present invention may also be used to reduce perspiration, sweating, or hyperhydrosis from eccrine (sweat) glands or apocrine glands. A preferred embodiment of the present invention may be used to treat other skin disorders such as, for example, viral warts, psoriasis, precancerous solar keratosis or skin lesions, hyperhydrosis/ excessive sweating, aging, wrinkled or sundamaged skin, and skin ulcers(diabetic, pressure, venous stasis).

Scarring is commonly seen as a consequence of disorders, diseases, or dysfunctions of the sebaceous or hair apparatus. Scarring may consist of one or more of the following: raised hypertrophic scars or fibrosis, depressed atrophic scars, hyperpigmentation, hyperpigmentary redness or telangectasia and hair follicle related scarring. Photomodulatory, photochemical, or photothermal treatments alone, or in combination with exogenous or endogenous chromophores, or combinations thereof, can be used simultaneously, sequentially, etc., as described herein for the treatment of various disorders, diseases, or dysfunctions. Further, as herein described, the term photomodulation refers to the treatment of living tissue with light along, heat emitted by a light source, or light-activated chemical compositions, or any combination thereof. Falling within the scope of photomodulatory treatments are photothermal treatment, photoactivation, photoinhibition, and photochemical treatment of living tissue and, in particular, hair related structures within human or animal skin. Further, electromagnetic emitters of the present invention can fall into three categories: those which emit light in the visible spectrum and are useful for photoactivation and photoinhibition photomodulatory process; those that emit light in the ultraviolet spectrum and are also useful for photoactivation and photoinhibition photomodulatory process; and those that emit light in the infrared region and permit photomodulation treatment to be carried out through photothermal means, i.e., heat activation of the exogenous chromorphore, living cells or tissue, or both.

A preferred embodiment of the present invention may use various microencapsulation processes to deliver active agents. If the diameter of the micro encapsulations is less than five microns, then there may be relatively site specific delivery into the structures. If the diameter of the microencapsulations is in the range of about one micron, then the active agents may be delivered with a more random distribution between the hair ducts and the oil glands. If the diameter of the microencapsulations is larger, on the order of about 20 microns or greater, then delivery will tend to be restricted primarily to the skin surface. Smaller diameters such as nano particles may be desirable. The micro encapsulations may be synthetic or natural. If ultrasound is used to enhance penetration, then the diameters and ultrasound treatment parameters may need to be adjusted according to the applicable principles which allow the estimation of the optimal ultrasound parameters for driving small particles into the skin, skin appendages or skin orifices. Larger molecules or proteins (including many reveuant growth factors) that cannot penetrate intact skin may be delivered by removing a portion of the stratum corneum or using ultrasound (or both) to enhance delivery.

Microencapsulation may be used to improve delivery of known agents such as chlorophyll, carotenoids, methylene blue, indocyanine green (ICG) and particles of carbon or graphite. A known technique for using a laser to produce a wavelength that may be absorbed by indocyanine green for a hair removal treatment process is described, for example, in U.S. Pat. No. 5,669,916, which is incorporated by reference. It has been found that by using smaller particles and putting the smaller particles into more uniform diameter microencapsulations, more site specific or uniform targeting may be achieved. A preferred formulation may include indocyanine green or other dyes or agents to form a lipid complex which is fat-loving (lipophilic). The delivery and clinical effects of agents and dyes such as indocyanine green dye may be refined and enhanced by selecting a carrier or encapsulation having a diameter that increases the probability of preferential delivery to a desired space, and/or that enables interaction with ultrasound to thereby increase the probability of preferential delivery, and/or that selectively attaches to the hair, duct, supporting tissues, hair shaft itself or bacteria, yeasts, or other organisms residing within these tissues.

Indocyanine green dye is presently in medical use, appears to be relatively benign, may be activated by red visible lasers, or other source of monochromatic or multichromatic light, (in the 800 nm range) may penetrate deeply enough to reach the oil glands, is used for leg vein and hair removal, and is relatively safe, cheap, and reliable. A known technique for using a laser to produce a wavelength that may be absorbed by indocyanine green for use in a leg vein treatment process is described, for example, in U.S. Pat. No. 5,658,323, which is incorporated by reference. Methylene blue has also been used according to the present invention with good success.

The microsponges containing the active agent may selectively attach, or at least have a chemical affinity for, some part of the oil gland. The ICG may be conjugated with lipids, which would then have an affinity for the hair by oil glands. Alternatively, the attachment may occur after the active agent is released from the microsponge, either passively or by attractive or chemical forces. In the case of some microencapsulation carrier vehicles, release may occur after disruption of the vehicle integrity itself, possibly by ultrasound or laser or light or other energy source or perhaps a chemical reaction.

In a preferred embodiment the ICG may be mixed with lipids, or put into microsponges (a.k.a. microspheres), and then applied to the skin surface, allowed to sit for a time. Excess dye may be removed, and then the area may be treated with laser light at about 800 nm, between about 0.1 and 100 millisec pulses and around 1.0 microJoule/ cm$^2$–10.0 Joules/cm$^2$. A treatment session lasting from about 1 second to about 15 minutes is preferred.

U.S. Pat. No. 5,817,089 specifies "particles having a major diameter of about 1 micron". It has been discovered, however, that such diameters may not be optimal. A 1993 Pharmaceutical Research journal article by Rolland et al describes an acne treatment wherein a topical acne drug is delivered with less irritation by putting the drug into synthetic polymer microsphere sponges. This article reported that an optimal diameter for site-specific delivery into sebaceous oil glands in the skin was about 5 microns, and that 1 micron particles randomly delivered to the hair follicle and stratum corneum.

Most agents may not inherently be the optimal size. However, virtually any agent may be preferentially delivered to the sebaceous glands by either synthetic microspheres, or liposomes, or albumen microspheres, or other similar "delivery devices".

In a preferred embodiment for stimulation of hair growth, graphite particles having an average diameter of about one micron or less may be carried in delivery devices, such as microsponges. The microsponges may then be suspended in a lotion. Ultrasound may be used to drive the particles into the skin. The optimal ultrasound parameters may be based on the outside particle diameter (especially if particles are uniform). Selective delivery of the particles to hair and perhaps to oil or gland sweat glands may be improved.

Use of such applications could enable selective delivery of agents which stimulate hair growth, or other hair treatments, to thicker, darken, color, lengthen hair where the encapsulation diameter was used, with or without ultrasound, to preferentially deliver, and ultrasound at different parameters or light or laser was used to release (not necessarily to activate or interact).

These techniques may be applied to many other agents in addition to ICG and graphite lotions. The term "encapsulated delivery device" is used herein as a generic term which encompasses all such possible items.

Pressure may be used to impel particles (i.e., graphite, carbon, or other active agent or skin contaminant particulates) into the skin, either in the spaces between the stratum corneum, into the hair ducts and hair follicles, hair bulge, hair stem cells (i.e., the hair structure), the sebaceous oil glands, or other dermal structures. Air pressure or other gases or liquids may be used to enhance delivery or increase the quantity of delivered agent. A known technique for using an air pressure device for removing skin surface is described, for example, in U.S. Pat. No. 5,037,432, which is incorporated by reference.

Ultrasound may be used to physically deliver hair dye and to enhance penetration into the hair shaft itself (see, for example, U.S. Pat. No. 5,817,089, incorporated herein by reference). The use of ultrasound to physically drive graphite particles down for the treatment of unwanted hair or acne appears to have been suggested in the prior art. However, the applicant is aware of no prior art disclosure or suggestion of: (1) the use of ultrasound to enhance the penetration of an agent into the hair shaft itself, or into surrounding cells; (2) the use of ultrasound to drive graphite particles into spaces between the stratum corneum to enhance the effects of a skin peel process (which physically removes a portion of the outer layers of the skin surface); or (3) physically removing the hair by methods such as waxing or pulling and then injecting the treatment composition, i.e., the chromophore or other topical composition, into the sebaceous gland or duct. Such methods are contemplated in one embodiment of the invention.

Further, it is contemplated that yellow light can be used to normalize melanin production in the skin. While not wishing to be bound by theory, it is believed that light in the yellow portion of the spectrum 590 nm to 660 nm red enhances the release of intermediary chemical signals that causes melanocyte cells to function more normally. That is, if the melanocyte cells are not working they begin to make pigment again; and if the melanocyte cells are producing too much pigment or producing the wrong configuration of pigment, they are stimulated to producing pigment in the correct amount and configuration.

A known skin peel process may be improved by using ultrasound to open intercellular spaces in the outer stratum corneum layer of the skin via cavitation. Then an active agent may be driven in further with the same or similar ultrasound. Fibroblast stimulation may be optimized with both topical agents that are applied afterwards (while the skin is still relatively permeable) and also with additional low level light stimulation.

The processes described above may be used to deliver two different agents, either serially or simultaneously. The two agents may then be activated by the light source together to work synergistically, or to combine and then have an effect, or to deliver two different agents that may be activated simultaneously or very closely in time. Two different light sources or wavelengths may be used serially or simultaneous to have different effects such as treating active acne lesions and also acne scarring; treating acne rosacea lesions and allows rosacea blood vessels or telangectasia; or using photothermal means for active acne and nonthermal photomodulation for treating acne scarring or skin wrinkles.

Two entirely different laser, LED, or light beams may be delivered substantially simultaneously through the same optics at different parameters. For example, one beam may be delivered primarily to release or to activate or precondition, and a second beam primarily to treat. Additive effects may be achieved by using two beams at the same time, such as the use of blue light with a wavelength of approximately 400 nm and red light with a wavelength of approximately 600 nm. For example, a known process for skin peel and hair reduction may be optimal at 1064 nm for safety and for treating all skin colors, but other wavelengths may be better to achieve a low level laser stimulation of fibroblasts. Acne reduction is achieved by this process, as well, using lasers or LEDS as the low-level light source at a wavelength chosen according to the absorption spectrum of the topical composition used. Particularly preferred for topical compositions are those comprising hair or vascular growth factors or hormones and derivatives thereof, and mixtures thereof, as well as derivatives, analogs, and genetically engineered forms of such agents as well ornithine decarboxylase stimulators.

A hand-held device containing the low-level light source may be used to photomodulate or photothermally activate, or both, the living tissue or active ingredient in the topical composition, or both, for skin peel, hair growth stimulation, or hair thickening, or increase hair density, hair growth rate, restore or alter hair pigmentation, hair shaft thickness, and either simultaneous or synchronized sequentially in time to deliver another wavelength that may be optimal in view of the absorption characteristics of the patient's fibroblast spectrum, the hair structure or the absorption spectrum of the topical composition. In one case it may also be the best wavelength to stimulate mitochondria or fibroblasts. In another case it may allow selection of a melanin or dye (or other agent) having very strong affinity for the sebaceous gland or hair structure and a very strong absorption at the wavelength used for treatment. The various embodiments of the invention described herein are also well-suited to the stimulation, proliferation, and growth of hair implants and transplants.

There are a wide variety of different operating parameters that may comprise conditions effective to produce beneficial cellular effects such as triggering cellular regeneration or photoactivation or photostimulation of hair growth. Further photothermal modulation of the hair and surrounding tissue can be accomplished via the same means as described above, although the operating parameters may vary. The difference being that photothermal treatment uses heat to induce minor to moderate amounts of thermal injury to the hair or surround tissue to stimulate the activity of the target tissue.

Exogenous chromophores are substances which absorb light or electromagnetic radiation in at least one narrow band of wavelengths and assist with the treatment method and system of the present invention by applying them to an area of the skin to be treated. Selection of the exogenous chromophore is determined by the absoroption spectra of the chromophores and is dependent on the wavelength of the narrowband multichromatic emitter used for treatment. In accordance with a preferred embodiment of the invention, the chromophore will aid in treatment by enabling at least the dominant or central wavelength of the narrowband, multichromatic radiation to penetrate at least the stratum corneum layer of the skin and permitting the photomodulation or photothermal injury or destruction of living tissue, hair, duct, or supporting tissue in and below the stratum corneum. In some instances, the photomodulated tissue can be below all of the epithelial layers of the skin.

Some examples of possible operating parameters may include the wavelengths of the electromagnetic radiation to which the living tissue containing cells to be regenerated, stimulated, inhibited, or destroyed, the duration of pulses (pulse duration) of the electromagnetic radiation, the number of pulses, the duration between pulses, also referred to as repetition rate or interpulse interval. Intervals between treatments can be as long as hours, days, weeks, months, etc.; and the total number of treatments is determined by the response of the individual patient. Further, treatment regimens using a combination of more than one wavelengths either simultaneous or in sequence may be used. As well, the energy intensity of the radiation as measured at the living tissue (typically measured in Joules per centimeter squared, watts per centimeter squared, etc.), the pH of the cell, tissue or skin, the skin temperature, and time from application to treatment with a light source, if used with exogenous chromophore (which can be topical, injected, driven in with ultrasound, or systemic) is determined by the nature of the treatment and is further illustrated in the Examples.

Figure 6:
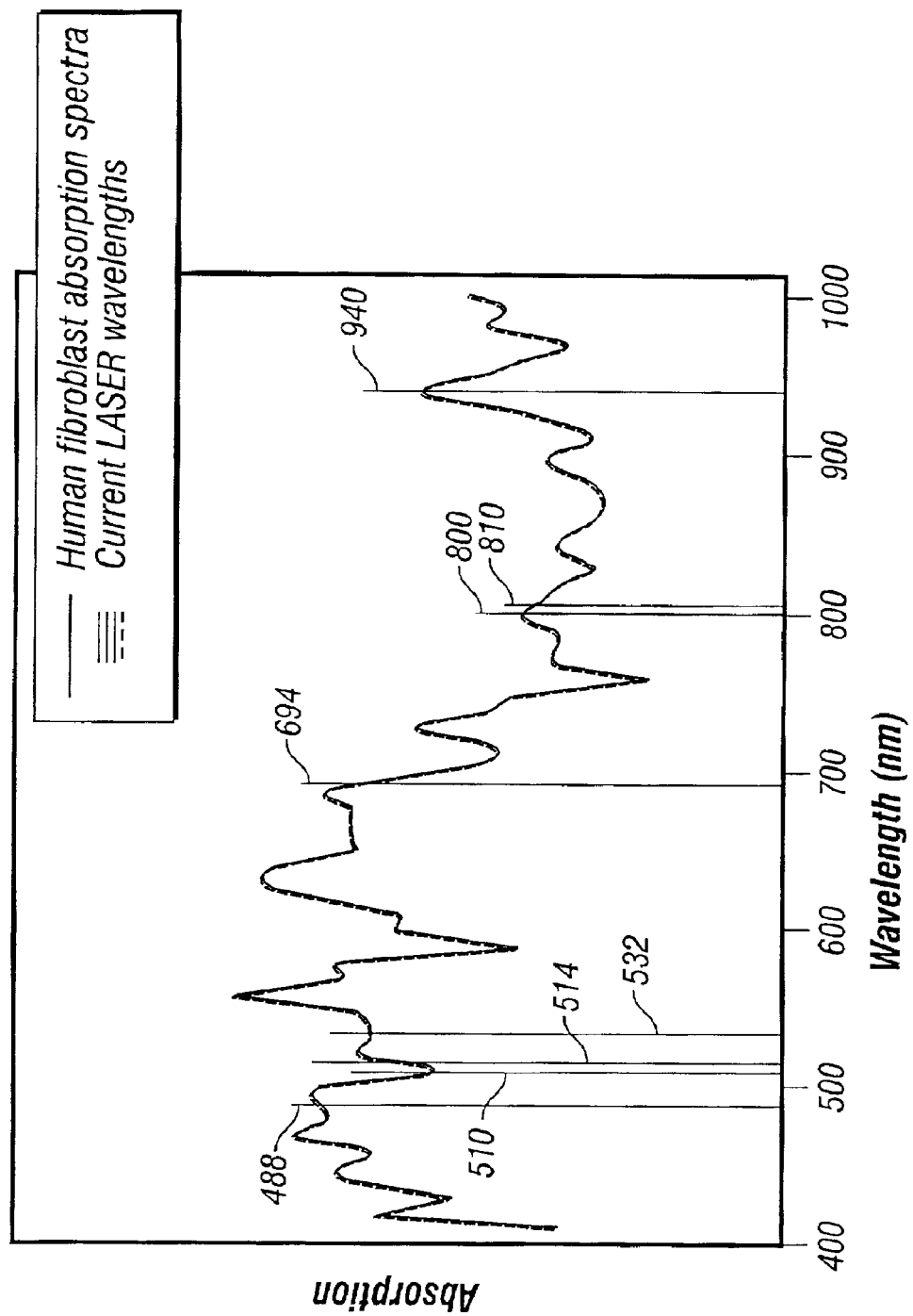
FIG. 6 is a graphical illustration of the absorption spectrum of human fibroblast overlayed with the wavelengths used by laser emitters.
Figure 7:
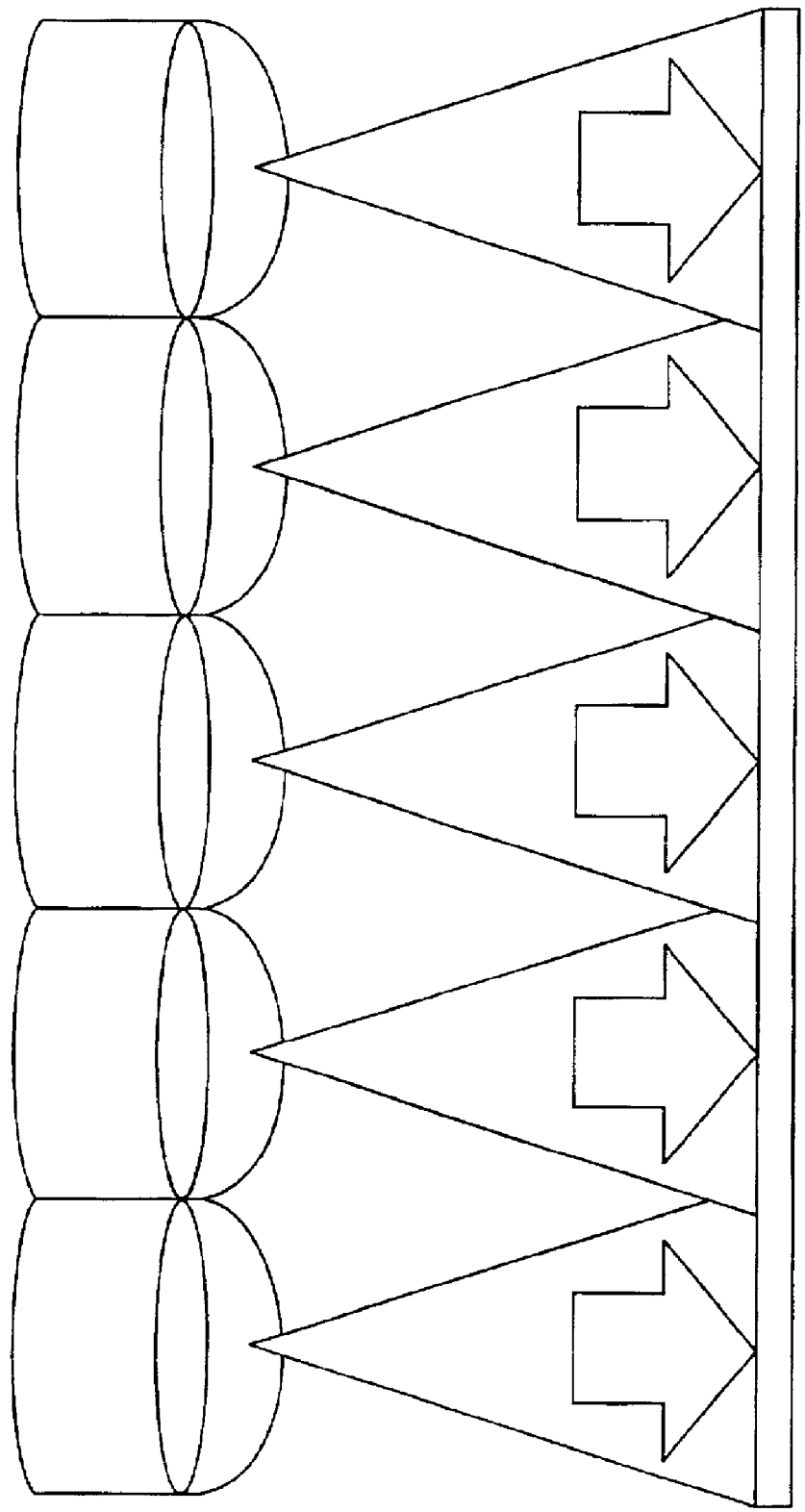
FIG. 7 illustrates in perspective the spacing of the optoelectronic devices of the present invention in close packed spacing in one dimension.
Figure 8:
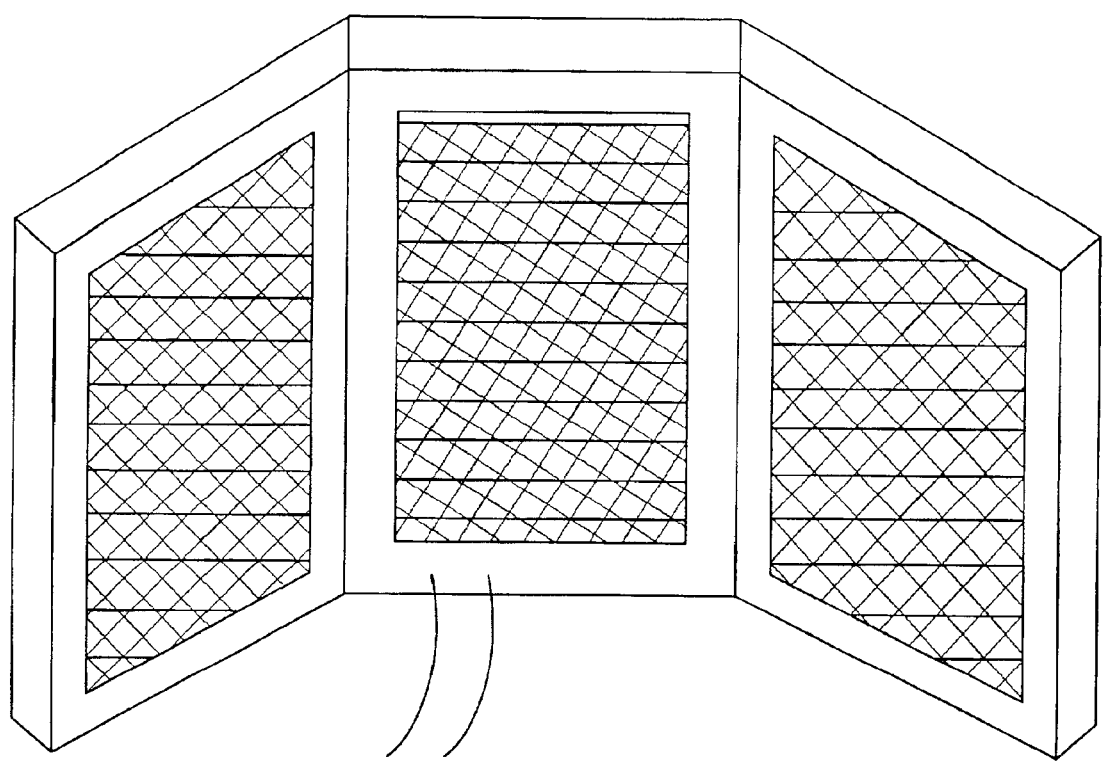
FIG. 8 show an array of optoelectronic devices arranged into three panels. The cross hatched areas represent protective covers. The covers may transmit light or may diffuse light. The set of three panels shown are hinged to allow adjustment, so that the arrangement resembles a three panel make-up mirror.

Wavelength—Each target cell or subcellular component, or molecular bond therein, tends to have at least one unique and characteristic "action spectrum" at which it exhibits certain electromagnetic or light absorption peaks or maxima FIG. 6, for example, shows the absorption spectrum of one line of human fibroblast cells in monolayer tissue culture. Different cell lines (of the same cell—for example fibroblasts from 3 different patients) exhibit some differences in their absorption spectra and thus using narrow band multichromatic light (rather than monochromatic light) is also useful in producing the optimal clinical effect. When these cells or subcellular components are irradiated with wavelengths corresponding to the absorption peaks or maxima, energy is transferred from the light photon and absorbed by the target. The particular features of the delivered energy determine the cellular effects. The complexity of these combinations of parameters has produced much confusion in the prior art. Basically, the wavelength should roughly correlate with an absorption maxima for the target cell or subcellular component or tissue, or exogenous chromophore. In some cases it may be desirable to target more than one maxima—either simultaneously or sequentially on the same or different treatment dates. The presence of multiple maxima action spectra are common for a given cell or subcellular component or exogenous chromophore and different wavelength maxima irradiation may produce different results.

If the wavelength band is overly broad, then the desired photomodulation effects may be altered from those intended. Consequently, use of broad band noncoherent intense light sources may be less desirable than those specified for use with the present invention, in contrast to the use of multiple narrowband emitters. The laser diodes are also multichromatic with narrow wavelength bands around a dominant band, i.e., they are narrowband multichromatic devices— devices which emit electromagnetic in a narrow band of radiation either symetrically or asymetrically around a dominant wavelength. For purposes of the present invention, any device that emits electromagnetic radiation in a bandwidth of +/− about 1000 nanometers around a dominant wavelength can be considered to be a narrowband, multichromatic emitter. LEDS, while not monochromatic, emit in such a narrow band as to be considered narrowband multichromatic emitters. The narrow band allows photons of slightly different wavelengths to be emitted. This can potentially be beneficial for creating certain desirable multi photon interactions. In contrast, most commercial lasers emit light at a single wavelength of light and are considered monochromatic. The use of lasers, according to the prior art, has relied upon the coherent, i.e., monochromatic, nature of their electromagnetic emissions.

Wavelength may also determine tissue penetration depth. It is important for the desired wavelength to reach the target cell, tissue or organ. Tissue penetration depth for intact skin may be different than the tissue penetration depth for ulcerated or burned skin and may also be different for skin that has been abraded or enzymatically peeled or that has had at least a portion of the stratum corneum removed by any method. It is also important to penetrate any interfering chromophore that also absorbs at this same wavelength (e.g. dark ethnic skin, plastic Petrie dishes for tissue or cell culture, etc.). It is important to penetrate any tissues or organs in its pathway.

For example, light having a dominant wavelength emission in the range of about 400 nm to about 420 nm has such a short wavelength that not all sebaceous glands or acne cysts can be effectively treated due to the limited depth of penetration of the radiation, whereas light having a wavelength of about 600 nm to about 660 nm can more easily penetrate to a greater depth, if treatment of the lower dermal layers or even deeper is desirable. Accordingly, the selection of the dominant wavelength of the radiation emitter is also dependent on the depth of treatment desired. The selection of the proper wavelength is one of the significant parameters for effective use of the present invention, but others are important as well. To achieve treatement according to the present invention, the following are the relevent parameters that must be chosen and applied to the emitter for electromagnetic radiation in order to photomodulate any cell signaling pathways leading to the stimulation or inhibition of gene expression which directly or indirectly modulates hair growth. Specifically, these parameters are:

Energy Density—The energy density corresponds to the amount of energy delivered during irradiation and is also referred to as energy intensity and light intensity. The optimal 'dose' is affected by pulse duration and wavelength—thus, these are interrelated and pulse duration is very important—in general high energy produces inhibition and lower energy produces stimulation.

Pulse duration—The exposure time for the irradiation is very critical and varies with the desired effect and the target cell, subcellular component, exogenous chromophore tissue or organ.(e.g. 0.5 microseconds to 10 min may be effective for human fibroblasts, though greater or lesser may also be used successfully).

Continuous Wave (CW) vs. pulsed—e.g. the optimal pulse duration is affected by these parameters. In general, the energy requirements are different if pulsed mode is used compared to continuous (CW) modes. Generally, the pulsed mode is preferred for certain treatment regimen and the CW mode for others.

Frequency (if pulsed)—e.g. higher frequency tends to be inhibitory while lower frequency tends to be stimulatory, but exceptions may occur.

Duty cycle—This is the device light output repetition cycle whereby the irradiation is repeated at periodic intervals, also referred to herein as the interpulse delay (time between pulses when the treatment session comprises a series of pulses).

Suitable active agents for use in topical compositions applied to the skin in accordance with the present invention include one or more of Vitamin C, Vitamin E, Vitamin D, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, algae, an antioxidant, a phytoanthocyanin, epigallocatechin-3-gallate, a phytonutrient, plankton, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, minoxidil, finesteride, a hair growth stimulating substance, a hair growth inhibiting substance, a dye, a natural or synthetic melanin, a metalloproteinase inhibitor, an inhibitor of AP-1 or C-Jun or both, proline, hydroxyproline, an anesthetic substance, chlorophyll, bacteriochlorophyll, copper chlorophyllin, chloroplasts, carotenoids, phycobilin, rhodopsin, anthocyanin, and derivatives, subcomponents, immunological complexes and antibodies directed towards any component of the target skin structure or apparatus, and analogs of the above items both natural and synthetic, as well as combinations thereof.

In one embodiment of the invention, topical skin care formulations may be used for altering the pH or acidity of the skin.

In addition to being an effective treatment method for reducing and eliminating the presence of common acne bacteria such as acnes vulgaris and for safely treating conditions such as pseudofolliculitis barbae, acne rosacea, and sebaceous hyperplasia, the present invention also has application to the reduction of cellulite. Using any of the light sources suitable for use as described herein, adipocyte cells can be photomodulated. Modulation of adipocytes alone for fat reduction or to alter the condition termed cellulite can be made directly through death of the adipocytes, through increasing their metabolic rate, decreasing their storage of lipid, lipolysis or rupture. Such modulation or destruction can be accomplished through one or a combination of massage, vibration, ultrasonic cavitation, ultrasonic thermal heating, modulation of receptors or genes in adipocytes, modulation with any source or combination of sources of electromagnetic radiation alone or in combination with exogenous chromophores or topically applied or injected substances which stimulate or inhibit these processes. Photomodulation increases the local microcirculation in the cellulite and alters the metabolic activity of the adipocytes and supportingcells. Enhanced local microcirculation, metabolism or enzymatic activity, or combinations thereof, may be produced by photomodulatory means. To enhance the treatment, any of the topical chromophores as previously described can be used or non-chromophoric compositions can be used in conjunction with any of the photomodulatory methods, including low-intensity light therapy. Further photothermal means may be used to destroy adipocyte cells alone or in combination with photomodulatory means, with or without the use of exogenous chromophores.

Many living organisms—both animals and plants—have as one of their major defense mechanisms against environmental damage to their cells and DNA repair system. This system is present in many if not all living organisms ranging from bacteria and yeasts to insects, amphibians, rodents and humans. This DNA mechanism is one which is involved in processes to minimize death of cells, mutations, errors in copying DNA or permanent DNA damage. These types of environmental and disease and drug related DNA damage are involved in aging and cancer.

One of these cancers, skin cancer, results from ultraviolet light damage to the DNA produced by environmental exposure to natural sunlight. Almost all living organisms are unavoidably exposed to sunlight and thus to these damaging UV rays. The damage which is produced is a change in the structure of the DNA called pyrimidine dimers. This causes the DNA structure to be altered so that it cannot be read or copied any longer by the skin cells. This affects genes and tumor development and proper functioning of the immune system.

An enzyme called photolyase helps to restore the original structure and function of the damaged DNA. Interestingly photolyases are activated by light . . . to then act to repair the DNA damaged by ultraviolet light . . . In the dark it binds to the cyclobutane pyrimidine dimmer created by the UV light and converts it into two adjacent pyrimidines (no dimer connecting these any longer) and thus the DNA damage is repaired. This direct reversal of DNA damage is called "photoreactivation". The photolyase upon exposure to blue light absorbs the light energy and uses this energy to 'split' the dimer and thus restore the normal DNA structure. Other mechanisms of DNA repair exist as well.

The photolyase repair mechanism is not well understood at present, but naturally occurring or synthetic or genetically engineered photolyase from essentially any living organism source can be utilized for other organisms including human and veterinary and plant applications. DNA damage produced by factors other than ultraviolet light may also be repaired including, but not limited to, such factors as other environmental damage or toxins, radiation, drugs, diseases, chemotherapy for cancer, cancer, microgravity and space travel related damage, and a myriad of other causes.

Environmentally damaged skin and DNA can be treated with topical endonuclease compounds with, or without, the assistance of photomodulation. Preferably, penetration enhancing treatments such as ultrasound and others recited herein are used to maximize skin penetration of the endonuclease compounds.

The use of such naturally derived or artificially created or genetically engineered photolyase enzymes, endonuclease enzymes, or related enzymes or other proteins functioning for DNA or RNA repair have a wide variety of applications. For example, the ability to treat skin damaged by sunlight/ultraviolet light of disease and to repair, reverse, diminish or otherwise reduce the risk of skin cancer could be used either as a theraputic treatment or as a preventive measure for people with severely sundamaged skin, with precancerous skin lesions, or with skin cancer.

This principle applies not only to skin cells and skin cancer but to a very broad range of skin and internal disorders, diseases, dysfunctions, genetic disorders, damage and tumors and cancers. In fact potentially any living cells might have beneficial effects from treatment with photolyase or similar proteins in combination with light therapy. In one embodiment of the invention, the repair of damage to hair supporting structures may help to restore not only hair growth but also hair transplant growth and to reverse graying of hair.

While in nature the light to activate the photolyase typically comes from natural sunlight, essentially any light source, laser and non laser, narrow band or broader bandwidth sources can activate the photolyase if the proper wavelengths and treatment parameters are selected. Thus natural sunlight filtered through a selective sunscreen could be used to activate both native and exogenously applied photolyases. Another treatment option would be to apply the photolyase and then treat with a controlled light source exposure to the proper wavelength band and parameters. A wide variety of light sources could be utilized and the range of these is described elsewhere in this application. For example a low energy microwatt narrow band but multi-spectral LED light source or array with mixed wavelengths could be utilized. Particularly important is the wavelength produces by the light source and not the source. Those skilled in the art will recognize that there are many sources for electromagnetic radiation capable of producing the required wavelengths used in the various embodiments of the present invention.

Another embodiment is a filtered metal halide, halogen, or fluorescent light source with a dominant wavelength of 415 nm +/−20 nm and an exposure of 1–30 minutes at 1–100 milliwatts output can be utilized. Such exposure would occur minutes to days after application of a topical product containing photolyase. When used alone, the wavelength of light (in the blue portion of the visible spectrum) can be used to reduce skin wrinkles, repair photoaging in human skin and tissue, and activate natural photolyases. Moreover, this wavelength can activate other natural repair mechanisms to reduce vein and capillary visibility, normalize melanin and pigment product, and restore natural skin coloration.

Another example would be the repair of cells in the skin which have environmental damage but instead of repairing the cells which lead to skin cancer the cells which lead to aging (photoaging) of the skin are targeted for this therapy. In one embodiment, kin fibroblasts which have been sun damaged are treated with a photolyase and subsequently the photolyase is photomodulated with blue light to set in motion the DNA repair mechanism of photolyase—that is photoreactivation. This allows the repair of the structure and thus the normal functioning of the fibroblast DNA thus allowing normal functioning and proliferation of these fibroblasts—which produce the proteins such as collagen and elastin and hyaluronic acid and matrix ground substance which cause skin to be firm and elastic and youthful in appearance—thus producing anti-aging or skin rejuvenation effects in the skin as well as improving the structure and healthy function of the skin.

Various cofactors which are involved in this photoreactivation process can also be added either topically or systemically to further enhance or improve the efficiency of this process. Other cofactors needed in the production of these proteins once the cells recover normal function also may be added topically or systemically to enhance the anti-aging or skin rejuevenation process. The delivery of both the photolyase and/or the cofactors described above can be enhanced by utilizing ultrasound to increase skin permeability or to increase transport across the skin barrier and into the skin and underlying tissues. Removal of a portion of the stratum corneum of the skin can also be used, alone or incombination with ultrasound, to enhance penetration and delivery of these topically applied agents. Additionally such methods of removing or altering the stratum corneum can assist in penetration of the light or the efficiency of same or allow use of lower powered light sources including home use devices such as battery powered LED sources.

A variety of sources exist for obtaining photolyases. These may include native naturally occurring photolyases, compounds derived from other living organisms (that is one may use for example bacterially derived, or yeast derived, or plankton rederived, or synthetic or genetically engineered, etc., photolyases and use them in human skin for beneficial effects thus not limited to same species derived photolyases. One known photolase is derived from *Anacystis nidulans* while others can be derived from bacteria—yeast in fact protect themselves with a photolyase which can be used in humans, other microorganisms, plants, insects, amphibian and animal sources exist.

The photolyase enzymes function by light induced electron transfer from a reduced FAD factor to the environmental exposure produced pyrimidine dimers. The use of free radical inhibitors or quenchers such as antioxidants can also be used to supplement the photolyase therapy. Other light activated chromophores may be utilized with light sources and properly selected parameters to further enhance, stimulate, photomodulate, photoactivate or photoinhibit the target or supporting cells or tissue to promote the most effective treatment.

There are many causes of free radical damage to cells. In one embodiment wound healing can be accelerated by utilizing a combination of antioxidants, cell growth factors, direct photomodulation (photoactivation) of cells, and photoreactivation through photolyases. Topical or systemic therapy with the proper cofactors and replacing any deficiencies of cofactors can further enhance wound healing. For example, a chonic leg ulcer wound could be treated with an antioxidant mixture of vitamin E, vitamin C and glutathione, as well as cofactors such as fatty acids and keto acids such as sodium pyruvate and low level light therapy using and LED array with parameters selected to photostimulate fibroblasts and epithelial cells could also receive treatment with a photolyase and blue light therapy with or without addition of various growth factors or subcomponents thereof thus greatly accelerating wound healing and healing wounds or bums that would otherwise not be treatable.

The potential uses of photolyases and light therapy include: the treatment or repair or reverse nerve damage or diseases including spinal cord injuries and diseases; cancer or cancer treatment related problems including radiation and chemotherapy; cervical dysplasia and esophageal dysplasia (Barrett's esophagus) and other epithelial derived cell or organ disorders such as lung, oral cavity, mucous membranes, etc.; eye related diseases including but not limited to macular degeneration, cataracts, etc.

There are very broad health and commercial applications of photolyase mediated photorepair or photoreactivation of DNA (or RNA) damage with flavin radical photoreduction/DNA repair via photomodulation or native or exogenously applied natural or synthetic or genetically engineered photolyases. The addition of topical. Oral, or systemically administered photolyases and also their cofactors or cofactors of the cells whose DNA is being repaired further enhance these applications. The use of oral antioxidant or photomodulation enhancing agents or synergistic cofactor supplements can also enhance the effects of photomodulation in any body tissue or cell treated. The enhanced delivery of such substances topically via ultrasound assisted delivery, via alteration of the skin's stratum corneum, and/or via special formulations or via special delivery vehicles or encapsulations are yet an additional enhancment to this process.

Additional research in this area has confirmed that people are affected by certain colors. For example, there are studies showing that blue and green are the most calming for paint in medical offices; and other studies showing that different tints of sunglasses affect moods. The colors red and orange, i.e., the brain's perception of light having a wavelength in the red and orange portions of the visible spectrum, have been shown to 'agitate' people.

There are also blue light photoreceptors such as cryptochrome which photomodulate the molecular clocks of cells and the biological or circadian rhythm clocks of animals and plants. It is believed that photomodulation of the pineal gland in the human brain can be achieved through the present invention and, as a result, therapies relating to the restoration and control of circadian rythms is contemplated in one embodiment of the invention, most preferably using blue light having a wavelength of between about 390 nm and 490 nm. These are the mechanisms that regulate responses to solar day/night rhythms in living organisms. These protein photoceptors include vitamin B based crytochromes. Humans have two presently identified cryptochrome genes which can be directly or indirectly photomodulated (that is photoactivated or photoinhibited) and more as yet undiscovered receptors may exist in the retina or the brain which may be stimulated (or even direct photomodulation of the brain itself).

The clinical applications include treatment of circadian rhythm disorders such as 'jet lag', shift work, etc, but also insomnia, sleep disorders, immune dysfunction disorders, space flight related, prolonged underwater habitation, and other disturbances of circadian rhythm in animals. Particularly noteworthy among potential disorders arising from disruptions or alterations in circadian rythms are indications that cancers, and particularly breast cancer, may be avoidable through careful control of "body clock" or circadian rhythm patterns. Circadian issues also exist for many other living organisms including the plant kingdom. Low-intensity light therapy of the present invention can be adapted for use to treat these afflictions, as well.

Warts can be treated using exogenous or endogenous chromophores with either photothermal or non thermal photomodulation techniques—or a combination of both. Examples of preferred embodiments of endogenous chromophores include the targeting of the vascular blood supply of the wart with either method. Anther preferred embodiment is the use of a topically applied or injected or ultrasonically enhanced delivery of such a chromophore into the wart or its blood supply or supporting tissues with subsequent photomodulation or photothermal activation of the chromophore. Immunological photomodulation may also occur with wart or infectious processes and such immunological photomodulation may be useful in treating a special subtype of hair loss called alopecia areata that is thought to be caused by immunologic disturbances in or around the hair structures thus causing hair loss that is not age related and which can cause profound psychological distress and can even result in the most severe cases in total loss of all body hair. Photomodulation can be utilized to stimulate regrowth of the hair in such alopecia cases.

One such example would be that of a chlorophyll topical formulation similar to those described elsewhere in this application but of higher concentration and vehicle and particle size optimized for wart therapy and the anaotomic location of the warts (for example warts on the thicker skin of the hand might be formulated differently than that used for vaginal warts). An LED light source could be used for home use with 644 nm in a battery powered unit wherein the topical formula was applied daily and treatment of individual warts was performed with the proper parameters until the warts disappeared.

For the situation of vaginal warts, a cyclindrical device with an array of LED arranged and optically diffused such that the entire vaginal cavity could be properly illuminated in a medically performed procedure would represent another embodiment of this therapy. A wide range of substances can be utilized either as the primary chromophore or as adjunctive supporting therapy. These compounds are listed elsewhere in this application. In another embodiment an immune stimulator is utilized in conjunction with photomodulation with or without an exogenous chromophore. In yet another embodiment a higher powered light source either narrow or broad band can e utilized with the same chromophore therapy as outlined above, but with parameters selected so that the interaction with the chromophore is non photomodulation, but rather intense photothermal effect so as to damage or destroy the wart but with minimal damage to surrounding uninvolved and non supporting tissues.

In one embodiment a chlorophyll and carotenoid topical formulation is applied and natural sunlight with or without a selective sunscreen are used to interact with the topical formulation. Another embodiment utilizes an injected or ultrasonically enhanced topical delivery of a dye or photodynamic theraputic dye or agent such as indocyanine green which has been used for vascular injections safely in other medical applications.

Papulosquamous, eczematous and psoriasiform and related skin disorders can be improved, controlled, reduced or even cleared by the same photomodulation or photothermal interaction with endogenous or exogenous chromophores. The process outlined for warts and the other disorders in this application may be used for such therapies. The use of ultrasound is particularly useful in the more scaly disorders in this group of diseases as are enzyme peels and other methods with gently remove scaling skin. Penetration of light into psoriasis presents for example a major problem with current therapies. Penetration of drugs and topical agents is likewise a major theraputic challenge. If the dry skin on top of psoriasis is removed it is well known that this stimulates further growth of the plaque or lesion of psoriasis—yet removal is needed to allow the drugs to penetrate and for light to penetrate. Currently almost all psoriasis light therapy is ultraviolet light and thus the risk of skin cancer and also of photoaging is very significant with a lifetime of repeated ultraviolet light therapy. Also such therapy typically involves treating large areas or even the entire body (standing in a large light therapy unit is like being in a tanning bed which is standing upright). Thus not only does the skin with psoriasis lesions get treated, but also all the normal uninvolved skin typically gets exposed to the damaging ultraviolet light.

Furthermore typical psoriasis treatments involve the use of oral drugs called psoralens. These drugs cross link DNA and are light activated. Thus DNA damage in produced not only by the ultraviolet light itself (like being out in sunlight but primarily ultraviolet A light), but in addition the psoralen drug produced DNA damage. Safety in children in an obvious concern as is use in pregnant or childbearing women.

The use of a topical light activated exogenous chromophore such as most of the agents listed in this application present no risk of DNA damage and also are generally very safe products—many are natural such as chlorophyll and can be safely used in children and pregnancy and child bearing age women. In addition the treatment is only activated where the topical agent is applied—unlike the use of oral psoralen drugs that activate not only the entire skin but also the retina and other tissues. The light used for this therapy is not only low in power, but it is for the most part visible or infrared light and is not ultraviolet—producing no DNA damage.

Thus the use of photomodulation or photothermal activation of exogenous light activated chromophores such as described herein represents a signicant advance in safety and efficacy.

The photolyase embodiments described above also have some application for diseases such as psoriasis. For some cases of psoriasis are very extensive covering large amounts of the surface area of the body and may be resistant to other known therapies. The application of a topical fomulation to the areas not being treated—or to all the body areas exposed to the traditional psoriasis phototherapy could receive a post treatment with the photolyase and blue light therapy—think of this as a type of 'antidote' to the ultraviolet psoriasis phototherapy wherein the repair of DNA damage to normal tissue was facilitated immediately following the psoriasis therapy—thus reducing significantly the risk of skin cancer and photoaging in future years.

Another embodiment involves the use of such a photolyase preparation in the evening after returning from a long day of occupational sun exposure or after an accidental sunburn. A spray or lotion containing the photolyase could be applied and then photorepair/photareacitvation of the acutely damaged DNA in the skin could be performed—and this could be performed with a large beam diameter home therapy unit—of by a white light source which contained enough of the desired wavelength or through selective filtering at the proper parameters to produce this reaction. Additionally an antioxidant skin formulation could be also applied to minimize erythema and other undesired effects of the sunburn. One such embodiment would be the preparation described earlier with a combination of vitamin C, vitamin E and glutathione and free fatty acids and one or more keto acids. A similar formulation could contain these agents but utilize only one or two of the three antioxidants listed.

In vitro fertilization processes can also be enhanced by photomodulation—with or without an exogenous chromophore. This can simply target the cells or subcellular components themselves, as described in the applicants copending U.S. patent application Ser. No. 09/894,899 entitled "Method and Apparatus for Photomodulation of Living Cells", which is hereby incorporated by reference in its entirety.

This can result in a greater success rate of fertilization and/or growth of embryos or other desirable effects on this process. In one embodiment an LED light source is used to treat sperm of animals or humans or genetically engineered embryos or subcomponents thereof to enhance fertilization. Hair structure cells grown in cell tissue culture can be photomodulated to multiply, differentiate (including turning stem cells into hair structure cells) or mature and develop prior to transplanting into the host skin. Such photomodulation can be continued after transplantation to enhance the survival of transplants as well as to enhance the growth rate and hair quality of such transplants.

In another embodiment photolyase or other photoreparative or light activated DNA repair proteins or substances combined with photomodulation can be utilized to 'correct' DNA damage in embryonic tissues thus generating a normal or more normal embryo. This can be performed in vitro or in utero (utilizing tiny fiber optic delivery of the proper light parameters—or the light can be delivered from outside the body into the womb without the risk of introducing a fiber optic device.

Another process in which photomodulation can be utilized for significant benefit is in the stimulation of proliferation, growth, differentiation, etc of stem cells from any living organism. Stem cells growth and differentiation into tissues or organs or structures or cell cultures for infusion, implantation, etc (and their subsequent growth after such transfer) can be facilitiated or enhanced or controlled or inhibited. The origin of such stem cells can be from any living tissue or organism. In humans stem cells for these embodiments may come from any source in the human body, but typically originate from the bone marrow, blood, embryo, placenta, fetus, umbilical cord or cord blood, and can be either naturally or artificially created either in vivo, ex vivo or in vitro with or without genetic alteration or manipulation or engineering. Such tissue can come from any living source of any origin.

Stem cells can be photoactivated or photoinhibited by photomodulation. There is little or no temperature rise with this process although transient local nondestructive intracellular thermal changes may contribute via such effects as membrane changes or structured conformational changes.

The wavelength or bandwidth of wavelengths is one of the critical factors in selective photomodulation. Pulsed or continuous exposure, duration and frequency of pulses (and dark 'off' period) and energy are also factors as well as the presence, absence or deficiency of any or all cofactors, enzymes, catalysts, or other building blocks of the process being photomodulated.

Photomodulation can control or direct the path or pathways of differentiation of stem cells, their proliferation and growth, their motility and ultimately what they produce or secrete and the specific activation or inhibition of such production.

Photomodulation can up-regulate or down-regulate a gene or group of genes, activate or inactivate enzymes, modulate DNA activity, and other cell regulatory functions.

Our analogy for photomodulation of stem cells is that a specific set of parameters can activate or inhibit differentiation or proliferation or other activities of a stem cell. Much as a burglar alarm keypad has a unique 'code' to arm (activate) or disarm (inhibit or inactivate) sending an alarm signal which then sets in motion a series of events so it is with photomodulation of stem cells.

Different parameters with the same wavelength may have very diverse and even opposite effects. When different parameters of photomodulation are performed simultaneously different effects may be produced (like playing a simple key versus a chord on a piano). When different parameters are used serially or sequentially the effects are also different—in fact depending on the time interval we may cancel out the prior photomodulation message (like canceling burglar alarm).

The selection of wavelength photomodulation is critical as is the bandwidth selected as there may be a very narrow bandwidth for some applications—in essence these are biologically active spectral intervals. Generally the photomodulation will target flavins, cytochromes, iron-sulfur complexes, quinines, heme, enzymes, and other transition metal ligand bond structures though not limited to these.

These act much like chlorophyll and other pigments in photosynthesis as 'antennae' for photo acceptor molecules. These photo acceptor sites receive photons from electromagnetic sources such as these described in this application, but also including radio frequency, microwaves, electrical stimulation, magnetic fields, and also may be affected by the state of polarization of light. Combinations of electromagnetic radiation sources may also be used.

The photon energy being received by the photo acceptor molecules from even low intensity light therapy (LILT) is sufficient to affect the chemical bonds thus 'energizing' the photo acceptor molecules which in turn transfers and may also amplify this energy signal. An 'electron shuttle' transports this to ultimately produce ATP (or inhibit) the mitochondria thus energizing the cell (for proliferation or secretory activities for example). This can be broad or very specific in the cellular response produced. The health of the cells and their environment can greatly affect the response to the photo modulation. Examples include hypoxia, excess or lack or ration of proper cofactors or growth factors, drug exposure (eg. reduced ubiquinone from certain anticholesterol drugs) or antioxidant status, diseases, etc. This is another circumstance wherein oral or systemic replacement of such agents or factors may be used to enhance the photomodulation effects. It should be also noted that any process which causes the accumulation of such agents—or conversely accelerates the inactivation or removal of inhibitors of such agents would have as a net outcome the effect of increasing the concentration of these agents without directly adding such agents.

The as yet unknown mechanism, which establishes 'priorities' within living cells, can be photomodulated. This can include even the differentiation of early embryos or stem cell population. Exogenous light activated chromophores may also be used alone or in combination with exogenous chromophores. Genetically altered or engineered stem cells or stem cells which have an inborn genetic error or defect or uncommon but desirable or beneficial trait may require a different 'combination' of parameters than their analogous 'normal' stem cells or may produce different cellular response if use the same combination of parameters. Using various methods of photomodulation or other techniques known in the art more specific cellular effects may be produced by 'blocking' some 'channels' that are photomodulated.

For example, consider an old fashioned juke box, if one selects the proper buttons one will set in motion a series of events resulting in the playing of a very specific and unique record or song. If however one were given a broom to push the buttons one would have to block all but the desired button to be selective. Likewise pushing an immediately adjacent button will not produce the desired outcome.

The magnitude of effects on cells may also be very dependent on the wavelength (when other parameters are the same). One such example is the contrast between irradiating chemical bonds in DNA with 302 nm light versus 365 nm light—the 302 nm light produces approximately 5000 times greater DNA pyrimidine dimers than the 365 nm only a short distance up the spectrum. Changing the wavelength can also convert the ratio or type of these dimers. Thus seemingly subtle changes in photomodulation or photochemical reaction parameters can produce very large and very significant differences in cellular effects—even at the subcellular level or with DNA or gene expression.

A final analogy is that photo modulation parameters can be much like a "morse code" to communicate specific 'instructions' to stem cells. This has enormous potential in practical terms such as guiding or directing the type of cells, tissues or organs that stem cells develop or differentiate into as well as stimulating, enhancing or accelerating their growth (or keeping them undifferentiated).

Another application of photomodulation is in the treatment of cellulite. Cellulite is a common condition which represents a certain outward appearance of the skin in certain anatomic areas—most commonly on the upper legs and hips which is widely regarded as cosmetically undesirable. Cellulite is the result of a certain anatomic configuration of the skin and underlying soft tissues and fat which may involve abnormalities of circulation or microcirculation or metabolic abnormalities—predominantly in the fat and supporting tissues. Photomodulation or photothermal treatments of the adipocytes (fat cells) or their surrounding supporting structures and blood supply alone or in combination can reduce the appearance of cellulite and/or normalize the structure and function of the tissues involved with the cellulite.

Photomodulation of adipocytes can be performed using endogenous chromophores suche as the adipocytes themselves, their mitochondria or other targets within the adipocyte electron transport system or respiratory chain or other subcellular components. Exogenous light or electromagnetically activated chromophores can also be photomodulated (photoactivated or photoinhibited) or photothermal interactions can also occur. Examples of such chromophores are listed elsewhere in this application and can be topically or systemically introduced into the target tissues or adipocytes or surrounding blood vessels. The use of externally or internally applied ultrasound can be utilized either to enhance delivery of the chromophore or to alter local circulation or to provide thermal effect or to provide destructive effect or any combination of these actions.

In one embodiment the chromophore is delivered into the fat layer under the skin on the thigh using external ultrasound to enhance skin permeability and also enhance transport. The alteration of the stratum corneum alone or in combination with the ultrasound can further enhance delivery of the chromophore. External massage therapy from various techniques can be used to enhance the treatment process. In another embodiment chromophore is injected into the fat layer prior o treatment with light. Some light therapy with or without ultrasound may be used to photomodulate or photothermally or ultrasonically increase or otherwise alter the circulation or microciruclation or local metabolic processes in the areas affected by cellulite or other tissues. The proper light parameters are selected for the target adipocytes, blood vessels, exogenous chromophores, etc. Since some of the target tissues in cellulite are deeper than for example wrinkles or acne, typically long enough wavelengths of light must be utilized so that the light penetrated deeply enough to reach the target tissue.

Various topical or systemic agents can also be used to enhance the cellulite reduction treatments. Some of these include various cofactors for the metabolic or adipocyte interactions described and have been previously described herein.

Some topical agents inhibit hair growth rather than stimulate hair growth. Hair growth inhibitors include inhibitors of ornithine decarboxylase, inhibitors of vascular endothelial growth factor (VEGF), inhibitors of phospholipase A2, inhibitors of S-adenosylmethionine. Specific examples of these, but not limited to, include licorice, licochalone A, genestein, soy isoflavones, phtyoestrogens, vitamin D, soy milk, inhibitors of nuclear factor kappa B (NF-kB), b3-AR adipocyte receptor, leptin, imiquinoid, urushiol, other topical or systemic immunomodulators, sulfhydryl compounds, free radical scavengers, antiandrogens, sulfones, heterocyclic esters and amides, and inhibitors of the metabolism of such agents, derivatives, analogs, conjugates, natural or synthetic versions or genetically engineered or altered or immunologic conjugates with these agents. Since VEGF molecules have a relatively large size, removal of some portion of the stratum corneum is helpful in enhancing penetration of the molecule into the skin. Smaller fragments of the VEGF molecule or peptides thereof may also be very beneficial in accordance with the present invention.

In a preferred embodiment, VEGF molecules, and fragments or peptides thereof are used in conjunction with ornithine decarboxylase for hair growth stimulation. Further enhancing the uses of these topical compositions is ultrasound application to maximize transdermal penetration. Finally, using low-intensity light therapy to photostimulate the hair growth structure within the skin is most perferred to further enhance treatment using VEGF with ornithine decarboxylase that has been permitted to penetrate into skin with the aid of ultrasound.

Additional compositions for enhancing hair stimulation alone, or in combination with low-intensity light therapy and the various means disclosed herein for enhancing penetration include: retinoids, retinol, minoxidil, finesteride, topical aldosterone antagonists, larrea divaricata, glutamine peptides, caffeine, phytoestrogens, tissue inhibitors of metalloproteinase (TIMP), antioxidants, grape seed extracts, green tea and derivates thereof, prevotella intermedia, lipopolysaccharides, nitric oxide generating agents, oxygen generating agents, polymixin, procyanidin B2, procyanidin C1, algae, yeast extracts, copper peptides, octylbutryate, capsicum, ginseng, niacinamide, soy, soy isoflavones, licorice, and genestin.

Also the same topical agents, exogenous light activated chromophores and treatments described for cellulite above also are hereby incorporated into methods for stimulating and/or inhibiting the growth of hair. Increasing the circulation or microcirculation of the hair bearing skin or skin structure may also be accomplished by simply producing vasodilation by any method known to those skilled in this art.

An alternative application of the present invention is to use light having a wavelength in the range of about 410 nm to 420 nm, or thereabouts. The use of blue light, in particular the 410–420 nm range can powerfully affect anti aging, stimulate collagen, and also remove, reduce, or normalize melanin pigmentation. This wavelength of light may also reduce or remove extra blood vessels in the skin most preferred for this type of application is the use of blue fluorescent light, although other light sources disclosed herein can be effective for such treatment. The benefit of fluorescent lights, of course, are that they are very inexpensive and do not require FDA approval for use. The treatment regimen includes a 10–15 minute exposure to the light source(which is up to 10 J/cm2 total dose for 15 minutes.) In an alternative embodiment, circadian rhythm treatment can be conducted using a similar treatment.

Another application of the present invention is for tattoo removal. The FDA has approved the use of very high-power lasers for this, but according to the present invention, long-pulsed lasers and other light sources at lower power can be employed to reduce or eliminate the appearance of tattoo inks in the skin with only a few, very short treatment sessions. In one embodiment of the invention, a home-use LED array, for example, can be employed at low power to reduce the visibility of tatoo inks. When used at a light intensity level of from 1 $\mu J/cm^2$ to 10 $J/cm^2$, a wavelength of 644 nm can produce significant reduction in the visibility of tattoo inks in treatment sessions lasting 0.1 to 100 minutes, suing either a continuous wave or 1 to 100 msec pulses with 1 to 100 msec interpulse intervals, repeated 1–20 times over 7–120 days.

Alternatively, long pulsed diode laser at 800–810 nm work with pulse durations in the 100–1000 millisec range, at from about 2–90 watts using an 8.0 mm beam diameter is useful in another embodiment of the invention, and this is for every color except red ink. For red tattoo inks, great success great success has been shown with pulses of 40 msec with a 595 nm pulsed dye laser. In another embodiment of the invention, multiple light sources with different wavelengths, usually a red and a yellow or red and green combination, can be used to remove all colors of ink during shorter, easier to control treatment sessions.

The present invention is further illustrated by way of the following examples.

EXAMPLE 1

Hair Growth Stimulation

Three patients with male pattern baldness are tested for stimulation of hair growth before and after receiving treatment in accordance with the non-ablative method of the present invention. Hair counts are taken from their scalp by utilizing subjective evaluations conducted by trained medical personnel. The LED treatment includes subjecting the target area of the patient's skin to a LED light having a pulse width of 250 msec and a pulse spacing of 250 msec for 90 pulses. Eight treatments over 12 weeks to the entire face with 590 nm multichromatic LED at an intensity ranging from 1.05–2.05 $\mu$Watts. Having a bandwidth of +/−5–15 nm, the LED therefore produces light in the wavelength range of from 575 nm to 605 nm. Further, the treatment maintains a skin temperature below the threshold of thermal injury. The average improvement in hair counts is shown in Table 1.

TABLE 1

| Hair Count | Pre treatments | Post treatments |
|---|---|---|
| Percent Improvement | 0% | 65% |

EXAMPLE 2

Hair Growth Stimulation—Pulsed Treatment

A team of blinded expert graders viewing before and after photos of patients subjected to the non-ablative LILT ("Low Intensity Light Therapy") of the present invention score the global improvement of hair thickness. Hair counting is also performed.

Six men with male pattern baldness were tested for hair growth stimulation and thickening of hair appearance. The LED treatment includes subjecting the target area of the patient's skin to a LED light having a pulse width of 10 msec and a pulse spacing of 100 msec for a period of 100 pulses. Eight treatments over 12 weeks to the entire face with 590 nm multichromatic LED at an intensity ranging from 1.0–2.0 µWatts. Having a bandwidth of +/−5–15 nm, the LED therefore produces light in the wavelength range of from 575 nm to 605 nm. Further, the treatment maintains a skin temperature below the threshold of thermal injury. The average increase in the appearance of hair density is shown in Table 2.

TABLE 2

| Week/Value | Averaged Value of Increased Hair Density |
|---|---|
| 0 weeks | 0% |
| 4 weeks | 6% |
| 8 weeks | 22% |
| 12 weeks | 54% |

EXAMPLE 3

Hair Growth Stimulation—Continuous Wave Treatment

One female with frontal hair loss is tested for hair growth stimulation in accordance with the procedures described in Example 2. Measurements by expert graders are taken from her scalp before and after treatment with a single continuous wave pulse for a total of 200 seconds from a 590 nm multichromatic LED at an intensity of 1.05–2.05 µWatts. Eight treatments spaced evenly over 12 weeks are administered to the patient's frontal scalp and forehead.

TABLE 3

| Week/Value | Averaged Value of Reduction |
|---|---|
| 0 weeks | 0% |
| 4 weeks | 12% |
| 8 weeks | 28% |
| 12 weeks | 43% |

EXAMPLE 4

Non-Ablative Skin Therapy for Hair Growth Stimulation

Pulsed Treatment

Human skin is exposed to 180 pulses of a narrowband, multichromatic 590 nm LED at an energy output of 1.05 microwatts to 2.05 microwatts with a pulse duration (the length of each pulse) of 20 milliseconds and an interpulse interval (time between each pulse) of 100 milliseconds. The treatment is repeated 8 times for 12 weeks to the entire faces of a group of 6 men with severe pattern hair loss. The amount of hair growth as measured by a team of blinded expert graders viewing before and after photos of the treated skin and making hair counts is shown in Table 4.

TABLE 4

| Treament Time (weeks) | Avg. % Increase in Hair Counts |
|---|---|
| 0 | 0 |
| 4 | 8 |
| 8 | 24 |
| 12 | 68 |

EXAMPLE 5

Non-Ablative Skin Therapy for Hair Growth Stimulation

Continuous Wave Treatment

Human skin is exposed to 200 second continuous wave of a narrowband, multichromatic 590 nm LED at an energy output of 1.0 microwatts to 2.0 microwatts. The treatment is repeated 8 times for 12 weeks to the entire scalp of a single male pattern baldness subject. The amount of hair growth as measured by a team of blinded expert graders viewing before and after photos of the treated skin is shown in Table 5.

TABLE 5

| Treament Time (weeks) | % Hair Growth Stimulation |
|---|---|
| 0 | 0 |
| 4 | 6 |
| 8 | 36 |
| 12 | 72 |

EXAMPLE 6

Non-Ablative Skin Therapy for Hair Growth Stimulation

Pulsed Laser Diode

Also suitable for use in accordance with the present invention is a laser diode. Typical pulse durations will be from about 100 milliseconds to about 1 second, for pulsed treatment, and from about 1 second to about 30 minutes for continuous wave treatment. Suitable operating power for the laser diode includes the range of from about 10 milliwatts to about 1 watt with about 200 milliwatts to 800 milliwatts being preferred. Commercially available laser diodes having a wavelength between 400 nm and 1000 nm can be used. For this example, human scalp skin is exposed to 90 pulses from an 810 nm laser diode at an energy output of 2.0 microwatts. An interpulse spacing of 100 milliseconds is used. The treatment is repeated 6 times for 12 weeks to the entire scalp of three males with scalp baldness. The amount of hair growth is shown in Table 6.

TABLE 6

| Treament Time (weeks) | % Reduction (cheeks measured) |
|---|---|
| 0 | 0 |
| 4 | 13 |
| 8 | 38 |
| 12 | 51 |

EXAMPLE 7

Hair Growth Stimulations—Pulsed Treatment

A team of blinded expert graders viewing before and after photos of patients subjected to the non-ablative LILT ("Low Intensity Light Therapy") of the present invention score the global improvement of receding frontal hairlines at the temples.

Eight males and one female are tested for hair growth stimulation. The laser diode treatment includes subjecting the target area of the patient's skin to a laser diode light having a pulse width of 400 msec using a 10 cm beam diameter and a pulse frequency of 1 hz (1 pulse per second). Three pulses are administered. Three treatments over 12 weeks to the frontal scalp and forehead with 810 nm laer diode at an intensity ranging 200 milliwatts/cm$^2$. Thermal injury is produced with blood vessels included among the target chromophores (but no skin wound care is needed). The average change in hair growth density is shown in Table 7.

TABLE 7

| Week/Value | Averaged Value of Hair Growth Increase |
|---|---|
| 0 weeks | 0% |
| 4 weeks | 18% |
| 8 weeks | 31% |
| 12 weeks | 34% |

EXAMPLE 8

Hair Growth Stimulation—Pulsed Treatment

A team of blinded expert graders viewing before and after photos of patients subjected to the non-ablative LILT ("Low Intensity Light Therapy") of the present invention score the global improvement of hair counts.

Six males with severe scalp boldness are tested for hair growth stimulation. The laser diode treatment includes subjecting the target area of the patient's skin to a laser diode light having a pulse width of 600 msec and a pulse frequency of 1 hz (1 pulse per second). Three pulses are administered. Six treatments over 12 weeks to the entire scalp with 940 nm laser diode with a 10 cm beam diameter at an intensity ranging 250 milliwatts/cm2. Further, this treatment produces a skin temperature sufficient to produce a non ablative thermal injury. The average hair count increase shown in Table 8.

TABLE 8

| Week/Value | Averaged Increase in Hair Counts |
|---|---|
| 0 weeks | 0% |
| 2 weeks | 8% |
| 7 weeks | 31% |
| 12 weeks | 40% |

EXAMPLE 9

Example 9 is carried out under identical conditions as Example 8, except that a 940 nm diode laser with a power of 10 microwatt/cm$^2$ exposes the subjects to twenty 50 millisecond pulses with an interpulse interval of 250 milliseconds. Six treaments over 12 weeks are performed with similar results. Mechanism is non thermal photoactivation.

EXAMPLE 10

Example 16 is carried out under identical conditions as Example 9 except that a 810 diode laser with a power of 2600 nanowatts/cm$^2$ and a beam diameter of 10 cm exposes the subjects to 60, 100 millisecond pulses with an interpulse interval of 100 milliseconds. Six treatments over 12 weeks are performed with similar results. The mechanism of action is non thermal photoactivation.

EXAMPLE 11

Example 11 is carried out under identical conditions as Example 10, except with a 940 nm diode laser with a power of 2 mW/cm$^2$ exposes the subjects to a continuous wave for 100 seconds. Four treatments over 12 weeks are performed with similar results. Photoactivation non thermal method is used.

EXAMPLE 12

Example 12 is carried out under identical conditions as Example 11, except with a 595 nm flashlamp pulsed dye laser with a power of 2.5 Joues/cm$^2$ exposes the subjects to 20 millisecond pulses, evenly spaced 4 weeks apart. Four treatments over 16 weeks are performed with similar results. Photothermal non ablative method.

EXAMPLE 13

Example 13 is carried out under identical conditions as Example 12, for the purpose of hair growth regeneration. A 595 nm flashlamp pulsed dye laser with a power of 6.0 Joues/cm$^2$ exposes the subjects to a single 40 millisecond pulse, evenly spaced 4 weeks apart. Five treaments over 20 weeks are performed. Hair density is increased by 42% and actual hair counts increased by 18%. Mechanism is thermal non ablative.

EXAMPLE 14

Example 14 is carried out under identical conditions as Example 13 for the purpose of hair growth stimulation. A 532 Nd:YAG laser with a power of 150 milliwatts/cm$^2$ and a beam diameter of 10 cm exposes the subjects to a single minimally overlapped 30 millisecond pulse, evenly spaced 4 weeks apart. Five treatments over 20 weeks are performed. Hair counts are increased by 28%. Method of thermal non ablative technique.

EXAMPLE 15

Example 21 is carried out under the same conditions on 5 male pattern baldness subjects for the purpose of hair growth stimulation. LED 590 nm at 50 msec pulses with 150 msec off time and 90 pulses. 8 treatments are performed at 1 week intervals and final assessment is made at 12 weeks. In addition to hair growth stimulation similar to Example 10 several other significant changes are noted including apparent 'restoration' of color to previously gray hairs and also apparent thickening of hair shafts.

EXAMPLE 16

Example 16 is carried out under identical conditions for the purpose of stimulating hair growth. Subjects have male pattern hair loss and are 20–40 years of age with no scalp diseases. A 644 nm LED device with a power of 2.2 microwatts/cm$^2$ exposes the subjects to 200 msec pulses with 200 msec off time between pulses for total of 50 pulses. Six treatments over 24 weeks are performed. Increase in appearance of hair growth is 22%.

EXAMPLE 17

Example 17 is carried out on female subjects with alopecia areata form of patchy hair loss in the scalp. A 940 nm diode laser with a power of 150 milliwatts/cm2 and a 10 cm diameter beam exposes the skin in the affected areas with continuous light for 4 minute exposures. Treatments are performed at 3 week intervals for 18 weeks. The alopecea areata lesions are reduced by 26% and spotty hair growth is observed in remaining bald patches.

EXAMPLE 18

Example 18 is carried out on acute hair loss from chemotherapy for the purpose of stimulating hair regrowth. A 623 nm LED array exposes a 7 inch by 10 inch rectangular area over the skin to 1.5 microwatts/cm$^2$ for 60 pulses of 100 millisec on time and 100 msec off time. Treatments are performed twice weekly until recovery of hair growth is accomplished. Recovery time is dependent on the severity of hair loss and reported eyelining of chemotherapy as well as other undetermined factors.

EXAMPLE 19

A series of cell tissue cultures containing monolayers of complete human hair follicles were treated in a comparison study to show the difference between treatment efficacy when conducted with a 595 nm pulsed dye laser and a 590 nm LED. The LED was at an energy intensity of 2 microwatts/cm$^2$, pulsed for 50 ms with a 100 ms interpulse interval. The non-thermal photomodulation treatment using the LED used 50 pulses. The 595 nm pulsed dye laser used a single pulse at an energy intensity of 2.5 Joules/cm$^2$ and a pulse length of 0.5 milliseconds for photothermal treatment. Analysis of hair shaft growth rate 5 days after treatment had been administered showed no significant change for the controls. The photothermal dye laser treated hair follicles exhibited a 12% decrease in hair shaft growth rate relative to the controls. The hair follicles treated with the non-photothermal photomodulation treatment of the present invention exhibited a 22% increase in hair shaft and growth rate relative to the controls.

I claim:

1. A method for stimulating hair growth, comprising:
   exposing a hair growth structure to a source of narrowband multichromatic electromagnetic radiation having a dominant emissive wavelength of from about 390 nm to about 1600 nm, without having applied a drug, cosmeceutical, and/or chromophore to the hair growth structure;
   photostimulating the hair growth structure by maintaining the exposure of the hair growth structure to the source of narrowband multichromatic electromagnetic radiation for a clinically effective duration and at a clinically effective light intensity to stimulate hair growth without causing skin ablation.

2. The method of claim 1 wherein said source of narrowband multichromatic electromagnetic radiation is selected from the group consisting of a light emitting diode, a laser diode, a mechanically filtered fluorescent light source, a mechanically filtered incandescent or filamentous light source, and combinations thereof.

\* \* \* \* \*

UNITED STATES PATENT AND TRADEMARK OFFICE
CERTIFICATE OF CORRECTION

| | | |
|---|---|---|
| PATENT NO. | : 6,936,044 B2 | Page 1 of 1 |
| APPLICATION NO. | : 09/986367 | |
| DATED | : August 30, 2005 | |
| INVENTOR(S) | : David H. McDaniel | |

It is certified that error appears in the above-identified patent and that said Letters Patent is hereby corrected as shown below:

In column 14, lines 22 - 26, replace the sentence:

"For purposes of the present invention, any device that emits electromagnetic radiation in a bandwidth of +/- about 1000 nanometers around a dominant wavelength can be considered to be a narrowband, multichromatic emitter."

with the following sentence:

-- For purposes of the present invention, any device that emits electromagnetic radiation in a bandwidth of +/- about 100 nanometers around a dominant wavelength can be considered to be a narrowband, multichromatic emitter. --

Signed and Sealed this
Eighth Day of November, 2011

David J. Kappos
*Director of the United States Patent and Trademark Office*